US012773690B2

(12) United States Patent
Anhold et al.

(10) Patent No.: US 12,773,690 B2
(45) Date of Patent: Oct. 27, 2026

(54) POINT OF CARE DEVICE

(71) Applicant: Abacuslabs Ltd., Ballinode (IE)

(72) Inventors: Heinrich Anhold, Ballinode (IE); Ruth Candon, Ballinode (IE)

(73) Assignee: Abacuslabs Ltd., Ballinode (IE)

( * ) Notice: Subject to any disclaimer, the term of this patent is extended or adjusted under 35 U.S.C. 154(b) by 869 days.

(21) Appl. No.: 17/924,844

(22) PCT Filed: May 14, 2021

(86) PCT No.: PCT/EP2021/062893
§ 371 (c)(1),
(2) Date: Nov. 11, 2022

(87) PCT Pub. No.: WO2021/229085
PCT Pub. Date: Nov. 18, 2021

(65) Prior Publication Data
US 2023/0211338 A1 Jul. 6, 2023

(30) Foreign Application Priority Data
May 15, 2020 (GB) .................................... 2007183

(51) Int. Cl.
*B01L 3/00* (2006.01)
*G01N 21/84* (2006.01)
*G01N 33/543* (2006.01)

(52) U.S. Cl.
CPC ........ *B01L 3/5023* (2013.01); *G01N 21/8483* (2013.01); *G01N 33/54388* (2021.08); *B01L 2200/025* (2013.01); *B01L 2200/04* (2013.01); *B01L 2300/0654* (2013.01); *B01L 2300/069* (2013.01); *B01L 2300/0825* (2013.01); *B01L 2300/168* (2013.01)

(58) Field of Classification Search
CPC ............. B01L 3/5023; B01L 2200/025; B01L 2200/04; B01L 2300/0654; B01L 2300/069; B01L 2300/0825; B01L 2300/168; G01N 21/8483; G01N 33/54388
See application file for complete search history.

(56) References Cited

U.S. PATENT DOCUMENTS 5,281,395 A * 1/1994 Markart ............ G01N 21/8483 356/243.1
6,750,962 B2 6/2004 Douglas
2004/0241752 A1* 12/2004 Anderson ............. G16H 15/00 435/7.1
2013/0162981 A1 6/2013 Emeric
2017/0023457 A1* 1/2017 Hart .................. G01N 15/1459
(Continued)

FOREIGN PATENT DOCUMENTS

EP 2861996 A1 4/2015
EP 3325153 A1 5/2018
(Continued)

OTHER PUBLICATIONS

International Search Report and Written Opinion for PCT/EP2021/062893 dated Sep. 17, 2021 (19 pages).

*Primary Examiner* — Dennis White
(74) *Attorney, Agent, or Firm* — Quarles & Brady, LLP

(57) ABSTRACT

A portable point of care device (1) for use in testing a biological sample, the device comprising: a sample collection member (4), a test cartridge (2), and a reader (220).

20 Claims, 15 Drawing Sheets

(56) References Cited

U.S. PATENT DOCUMENTS

| | | | | |
|---|---|---|---|---|
| 2017/0113221 | A1 * | 4/2017 | Hoffman | G01N 35/00069 |
| 2019/0317115 | A1 | 10/2019 | MacLean | |

FOREIGN PATENT DOCUMENTS

| | | | | | |
|---|---|---|---|---|---|
| WO | 2005090983 | A2 | | 9/2005 | |
| WO | 2014100725 | A1 | | 6/2014 | |
| WO | 2017015172 | A1 | | 1/2017 | |
| WO | 2020019014 | A1 | | 1/2020 | |
| WO | WO-2020016616 | A1 | * | 1/2020 | H04N 23/56 |

* cited by examiner

POINT OF CARE DEVICE

This application is a U.S. National Stage application, filed pursuant to 35 U.S.C. § 371, of international application no. PCT/EP2021/062893, filed on May 14, 2021, which claims the benefit of Great Britain Patent Application No. 2007183.3, filed May 15, 2020, the contents of which is incorporated herein by reference in its entirety.

FIELD OF THE INVENTION

The invention relates to a fluid collecting device and testing system. In particular, the invention relates to a point of care device for collecting bodily fluids and for testing the collected fluid, which is suitable for use in all healthcare settings including point of care settings that incorporate home use.

BACKGROUND TO THE INVENTION

Point of care (POC) testing generally involves medical diagnostic testing at or near the point of care, that is, at the time and place of patient care, generally by the bedside or beside the patient. POC testing also incorporates home testing, satellite testing or remote testing Most POC devices use membrane-based test strips using lateral flow (LF) principles. LF is a widely used medium for developing immunoassays in POC devices. Most LF devices detect a single biomarker and are typically semi quantitative. LF tests, such as the pregnancy test or a blood glucose test, provide a visual read zone where the formation of lines must be interpreted by the user, while others incorporate a single biosensor to more accurately determine analyte concentrations. These devices, due to their end use, often only require semi-quantitative detection and are developed for use in a single scenario with a single sample type. They are incapable of providing a POC analysis where a number of different biomarkers or metabolites can be measured simultaneously and quantitatively from the same sample application.

POC LF tests are associated with a number of challenges which have limited their use especially in the home settings and similar settings. These challenges include testing procedures which are challenging or burdensome for home users, compromised test performance and difficulty interpreting test results and/or communicating them to a clinician for further assessment.

In addition, test sensitivity and variation between tests are of concern for all people of skill in the art. Clinicians rely on test outputs to aid in diagnosis and to monitor patients including treatment outcomes. Trained professionals will not adopt POC testing as standard testing techniques unless laboratory comparable results are achievable. Similarly, home users require a POC platform that is sensitive, delivers reliable results and critically is easy to use. It is a regulatory requirement that manufacturers of self-test devices must consider the skills and means available to lay users and consider the impact of variation that can be expected in user's technique. Thus, there is a clear emphasis to ensure that POC tests aimed at home use are user friendly and pose low risk of user error in the handling of the device or interpretation of the results obtained. There is therefore a requirement for a POC testing platform that improves sensitivity and variation such that both skilled and non-skilled users are provided with a reliable testing platform.

LF qualitative tests give a simple yes/no result but provide no information about the severity of a condition or efficacy of treatment. Semi-quantitative results are broad and can overlap giving the user no new information when serial measurements or monitoring is required. Quantitative LF measurements are therefore required for these types of assessments.

LF tests have been contested as suitable for the early detection of disease due to issues with sensitivity particularly in the early stages of a condition where many analytes may not have elevated to a visually detectable level. This issue has been somewhat addressed by using these tests with electronic readers which reduce background noise and in doing so improve the limit of detection. However, even in these scenarios, larger, non-portable or minimally portable reading devices are required to enable test scanning and traceability functions. Quantification remains a challenge on pocket-sized, handled electronic devices which are more suited to POC settings.

In addition to LF challenges around ease of use, sensitivity and reliability, a secondary challenge with obtaining the quantitative result lies with taking the output of a LF test line and translating it into a digital signal which can be interpreted by the electronic reader and presented to the user in a reliable and reproducible way.

In human and animal clinical practice settings, prophylactic viral treatments often take the form of vaccines that are administered in a number of forms. Vaccine administration may be characterized by a spike in temperature and a change in biochemical parameters. Current methods to facilitate recognition of changes in blood parameters, including parameters of the host response, cannot be comprehensively performed at the POC due to a number of factors including skill required, size limitation, power supply, complex interpretation, communication capabilities and sampling limitations. No solution exists which would allow patients to monitor the relevant blood parameters in a home setting, allowing the identification of complications more quickly or providing confidence to the patient that the relevant blood biomarkers are within an acceptable range for the vaccine administered. This is also applicable more broadly for human health management where early detection of disease, assessment of clinical severity and monitoring routines would benefit from the availability of a sensitive, pocket-sized, easy to use device with multiplexing capability.

Such a device could be used to detect and quantify biomarkers of interest in the detection, assessment and monitoring of inflammatory and infectious diseases including viral and bacterial infection, autoimmune diseases and cancers.

In the case of bacterial and viral infections, the same symptoms of disease are often observed and are difficult to distinguish using simple methods available at the POC. In clinical practice it is important to identify the causative agent, as viral infections do not respond to antibiotic treatment. Viral infections frequently affect more than one bodily system at a time and are less frequently associated with inflammation and pain when compared to bacterial infection. However, these observations are the limit of differentiation that can be made without further in vitro assessment. Several organizations now recommend that antibiotics are not administered unless there is clear evidence of bacterial infection. Therefore, a tool that leads to a reduction in the number of viral conditions treated unnecessarily and/or an increase in the number of bacterial infections identified correctly immediately provides a valuable solution. Current rapid tests available for use at the point of care are limited with regards to the conscientious use of antibiotics by their inability to distinguish between infectious and non-infectious conditions in a single integrated, quantitative, and easily interpreted test. Furthermore, the devices and tests often described as rapid, are in fact small benchtop units which require a level of skill to operate, and which remove the ability to conveniently monitor a patient's response to treatment in real time.

WO 2017/015172 describes a sample collection device and a sample analysis cartridge which are received in a reader that includes a cartridge dock and housing. EP 2861996 describes a sample collection device, a cartridge, and a reader device. US 2013/0162981 describes a reader device for reading a test cartridge, wherein the reader comprises an optical imager that includes a sensor array and lens. WO 2005/090983 describes an analyte detection device for a point of care analysis system, comprising a cartridge and an optical detector.

It is an object of the present invention to overcome at least one of the above-referenced problems.

SUMMARY OF THE INVENTION

The invention relates to the development and provision of a POC testing platform that would be capable of analysing a number of biomarkers in the blood or other bodily fluid, which would present a number of positive outcomes. These positive outcomes include an increased uptake in POC testing in clinical and home use leading to more rapid decision making, clinical intervention and better patient outcomes. The invention also relates to methods for improving accuracy, precision and ease of use for point-of-care testing platforms. There is a need for a sensitive, pocket-sized, compact and easy to use LF reading device that enables rapid and reliable means for reading an LF test in multiple settings and that allows multiple assays to be run simultaneously whilst enabling sensitive analyte quantitation and meeting regulatory requirements in an minimally invasive way with respect to the user workflow and experience.

Devices such as the POC pocket-sized device of the claimed invention, when used in combination with appropriate biomarkers, will lead to a foreseeable reduction in unnecessary use of the already limited arsenal of antimicrobials available, rapid intervention in diagnosis and treatment of disease, and better health management at home and in a clinical setting. In certain settings, for example, a hospital, where the presence of infection is confirmed in a patient, the ability to use a testing platform to monitor a patient's response to antimicrobial therapy rapidly in real time would allow the professional to withdraw treatment at an earlier stage if necessary, thereby restricting the unnecessary use of antibiotics further. This method of use also allows the professional to change or augment the therapy if the patient's physiological response is not deemed satisfactory. In a home setting, a user can use the testing platform in combination with multiplexed biomarkers to determine health status and differentiate between a healthy physiological state and an unhealthy condition.

A POC appropriate, health screening and diagnostic pocket sized tool capable of detecting host response initiation, and assessing the severity and progress of the host response would be advantageous in a number of ways, e.g. the detection of subclinical infection before the onset of symptoms especially in cases where host response proteins may sometimes be the only indication of an immune challenge, rapid determination of the efficacy of treatment and earlier detection of a return to a normal physiological state.

Furthermore, a tool which has the features outlined above would be further improved in in cases where infection is determined by having the ability to further determine if the infection is a result of a viral or bacterial agent with a high degree of sensitivity and probability.

According to the present invention there is provided, as set out in the appended claims, a portable point of care device (1) for use in testing a biological sample, the device comprising: a sample collection member (4), a test cartridge (2), and a reader (220), the sample collection member (4) comprising a distal end (41), a sample chamber (42) and a proximal end (43) adapted to connect to the test cartridge (2); the test cartridge (2) comprising a housing (21) within which is a test strip (40), a distal end (23) and a proximal end (22), the proximal end (22) adapted to engage with the reader (220), as well as the proximal end (43) of the sample collection member (4); and the reader (220) comprising a casing (222) within which is housed an optical chassis stack (180), and a cartridge entry port (192) configured to accept the test cartridge (2); wherein the optical chassis stack (180) further comprises a first printed circuit board (PCB) 181, a lens holder (182), a lens (183), a second PCB (184), a chassis (185), a cartridge port (186) with springs (208), and a linear sensor array (189).

There is also provided a portable point of care device (1) for use in testing a biological sample, the device comprising: a sample collection member (4), a test cartridge (2), a reader (220), and an alignment pin (188); the test cartridge (2) comprising a housing (21) within which is a test strip (40), a distal end (23) and a proximal end (22), the proximal end (22) adapted to engage with a cartridge entry port (192) of the reader (220); the sample collection member (4) comprising a distal end (41), a sample chamber (42) and a proximal end (43) adapted to connect to the distal end (23) of the test cartridge (2); and the reader (220) comprising a casing (222) within which is housed an optical chassis stack (180), and the cartridge entry port (192) configured to accept the test cartridge (2); wherein the optical chassis stack (180) further comprises a first printed circuit board (PCB) (181) in communication with a lens holder (182), which accommodates a lens (183), a second PCB (184) in communication with the lens holder (182), a chassis (185) in communication with the second PCB (184), a cartridge port (186) with springs (208) in communication with the chassis (185), and a linear sensor array (189) in communication with the first PCB (181); wherein the optical chassis stack (180) further comprises a shaft (190) traversing therethrough from the first PCB (181) to the chassis (185), and configured to accommodate the alignment pin (188).

In one aspect, the sample collection member (4) further comprises a retractable piston (49) attached to the distal end (41) and accommodated within the sample chamber (42) such that when the retractable piston (49) is activated, a metered sample is obtained.

In one aspect, activation of the retractable piston is initiated by rotation of the distal end (41), wherein rotation of the distal end (41) disengages the distal end (41) from the sample chamber (42) and rotates the piston (49) out and away from the proximal end (43) of the sample receiving member (4). Preferably, rotation of the distal end (41) in a counter-clockwise movement disengages the distal end (41) from the sample chamber (42) and rotation of the distal end (41) in a clockwise movement re-engages the distal end (41) with the sample chamber (42).

In one aspect, the degree of rotation of the distal end (41) correlates to the volume of the metered sample obtained. Preferably, the distal end (41) rotates through 90°.

In one aspect, the distal end (41) is connected to the sample chamber (42) by an engagement member (45) and corresponding engagement member (44). Preferably, the engagement member (45) is selected from a threaded bore, a luer fitting or a snap-fit (80). Preferably, the engagement member (44) is selected from a corresponding threaded portion, a luer fitting or a snap-fit (80).

In one aspect, the proximal end (43) further comprises a sample conduit (48) configured to engage with either the test cartridge (2) or a sample delivery member of a vacutainer holder. Preferably, the sample conduit (48) is a needle, a capillary channel, a moulded vessel or a combination thereof.

In one aspect there is provided a reader (220) comprising a casing (222) within which is housed an optical chassis stack (180), and a cartridge entry port (192) configured to accept a test cartridge (2); wherein the optical chassis stack (180) further comprises a first printed circuit board (PCB) 181, a lens holder (182), a lens (183), a second PCB (184), a chassis (185), a cartridge port (186) with springs (208), and a linear sensor array (189). Typically, the lens (183) is a rod lens. The lens (183) may take the form of a series of tunnels forming a collimator into which the light travels. Light is thereby directed directly into the sensor array (189). The advantage being a concentration of reflected light. A further advantage is a reduction of interference from surrounding light. The benefit of using a rod lens is a reduction in focal distance and a reduction in the form factor.

In one aspect, there is provided a test cartridge (2) comprising a housing (21) within which is a test strip (40), a distal end (23) and a proximal end (22), the proximal end (22) adapted to engage with the reader (220).

In one aspect, the optical chassis stack (180) further comprises a shaft (190) traversing therethrough from the first PCB to the cartridge port (186), and configured to accommodate an alignment pin (188).

In one aspect, wherein the shaft (190) comprises at least three or four engagement means (190*a*, 190*b*, 190*c*, 190*d*), wherein the first engagement means (190*a*) is an aperture at the entrance to the shaft (190) on the first PCB 181; the second engagement means (190*b*) is also an aperture located on the second PCB (184); while the third engagement means (190*c*) and, optionally, the fourth engagement means (190*d*) are also apertures with a snap-fit configuration and are located on the chassis (185) that engage with the alignment pin (188).

In one aspect, the second PCB (184) comprises an aperture (202) and an illuminating light source (204). Preferably, the illuminating light source (204) sits below and to one side of the linear sensor array (189). Ideally, the light emitted from the light source (204) is directed to the test strip (40) at an angle via sloped sides on the cartridge window (24).

In one aspect, the cartridge (2) comprises a first machine-readable optical code (212) comprising timing data and a second machine-readable optical code (210) comprising a batch identifier.

In one aspect, the sensor array (189) comprises at least two optical readers in the form of a first optical reader and a second optical reader. Preferably, the first optical reader is configured to determine the speed that the test cartridge (2) is inserted into the reader (220) by reading and interpreting the first machine-readable optical code (212). Preferably, the second optical reader is configured to read and interpret the second machine-readable optical code (210) on the test cartridge (2).

In one aspect, the lens (183) is in the form of a lens array comprising two or more lenses. In one aspect, there are between about 20 and about 300 lenses in the lens array. Preferably, the lens array comprises between about 50 and about 200 lenses. More preferably, the lens array comprises between about 75 and about 150 lenses. More preferably, the lens array comprises between about 90 and about 125 lenses. Ideally, the lens array comprises about 100 lenses. Preferably, the lens (183) is a rod lens.

In one aspect, inner surfaces of the optical chassis stack (180) are coated with, or are partly formed with, a light-absorbing paint or a light-absorbing material.

In one aspect, the device further comprises a dilution chamber (6) adapted to nestle between, and engage with, the sample collection member (4) and the test cartridge (2), the dilution chamber (6) having a distal end (60), a proximal end (62) and a mixing chamber (63) therebetween adapted to receive a metered sample from the sample collection member (4).

In one aspect, the proximal end (62) is adapted to connect to the test cartridge (2) and the distal end (60) is adapted to connect to the sample collection member (4) by a plurality of snaps provided along the circumference of the ends (60,62). Preferably, the plurality of snaps (80) are adapted to matingly engage a lip (66) and a tab (66*a*) of the proximal end (62) with the proximal end (22) of the test cartridge (2).

In one aspect, the plurality of snaps are adapted to matingly engage with the sample collection member (4) at the distal end (60).

In one aspect, the mixing chamber (63) further comprises a dispensing chamber (68), wherein the dispensing chamber (68) is a hollow channel (69) having a plug (70) confined therein by means of an interference fit.

In one aspect, the distal end (60) comprises a seal (61). Preferably, the seal (61) is selected from a foil cover or a self-sealing seal.

In one aspect, the proximal end (62) further comprises a receptacle (64) adapted to receive a sample receiving member (25) of the test cartridge (2). Preferably, an inner diameter (67) of the receptacle (64) is smaller than an outer diameter (25*a*) of the sample receiving member (25). Ideally, the sample receiving member (25) further comprises a collection chamber (26) protruding upwards from the receiving member (25). Preferably, the collection chamber (26) comprises a sealed aperture (31), a sample holding area (30) within which is a baton (32) protruding upwards towards the sealed aperture (31) and a window (34). Ideally, the window (34) provides access to the test strip (40).

In one aspect, the collection chamber (26) is adapted to engage with the dispensing chamber (68) of the dilution chamber (6).

In one aspect, the collection chamber (26) is adapted to engage with the sample conduit (48) of the sample collection chamber (4).

In one aspect, when the sample collection member (4) is engaged with the dilution chamber (6), the sample conduit (48) pierces the seal (61) and delivers sample to the mixing chamber (63).

In one aspect, when the mixing chamber (63) is engaged with the test cartridge (2), the dispensing member (68) penetrates the sealed aperture (31) and dispenses a metered volume of sample to the sample holding area (30) and test strip (40).

In one aspect, the mixing chamber (63) further comprises an air bubble (72).

In one aspect, the dilution chamber (6) is configured to store a predetermined amount of a diluting solution to mix with the sample.

In one aspect, the test strip (40) comprises a sample pad, a conjugate pad, a testing membrane and a wicking pad. The conjugate pad is typically impregnated with a reagent capable of binding to the biomarker of interest. The testing membrane typically possess a capture region capable of binding the biomarker of interest. The wicking pad is assembled sequentially onto an adhesive backing card whereby the sample pad overlaps the conjugate pad, the conjugate pad overlaps the testing membrane and the wicking pad overlaps the testing membrane. The testing strip receives the test fluid from the sample pad and, through capillary action, flows through the length of the test strip from the sample pad; through the conjugate pad where the biomarker present in the sample reacts with the reagent; on to the testing membrane where biomarker-bound detection reagent binds to the capture region to produce a measurable signal; and finally to the wicking pad, which ensures fluid flow continues through the testing strip for the duration of the test runtime. The reaction occurs as the test fluid flows through the test strip.

In one aspect, the test strip (40) is impregnated with one or more reagents that react with one or more target molecules in the test sample. Preferably, the reagent is selected from an antibody, a labelled antibody, a nucleic acid, a labelled nucleic acid, a protein scaffold, a labelled protein scaffold, a peptide aptamer, a labelled peptide aptamer, an RNA aptamer, a labelled RNA aptamer, or a combination thereof.

In one aspect, the strip is a sandwich format and consists of a nitrocellulose membrane upon which an antibody to the target molecule and a control antibody have been immobilised.

In one aspect, the sample collection member (4) collects bodily fluid by capillary action, aspiration or under vacuum.

In one aspect, the test cartridge (2) further comprises at least one machine-readable optical code (210,212) encoding information that is read by the at least one optical reader in the linear sensor array (189). Preferably, result data from the test cartridge (2) can be transmitted to a remote device over a wireless communication means for display by the remote device.

In one aspect, the remote device is a mobile phone device or electronic tablet device.

In one aspect, there is provided a system for collecting and testing bodily fluid, the system comprising the device as described above.

In one aspect, there is provided a device for monitoring the immune status of an individual using the device as described above.

In one aspect, there is provided a device for assessing the infection status of an individual using the device as described above.

In one aspect, there is provided a device for predicting a health event in an individual using the device as described above.

In one aspect, there is provided a device for determining whether an individual is suffering from a disease using the device as described above.

In one aspect, the reader (220) further comprises a microcontroller and a memory coupled with the microcontroller, wherein the memory comprises executable program instructions to configure the microcontroller to perform the steps of: receiving by the reader (220) via a wireless communication means batch data from an application associated with the reader (220) residing on a mobile device; and storing the received batch data in the memory.

In one aspect, the batch data was obtained during manufacture of a batch of the test cartridges (2).

In one aspect, the reader further comprises: periodically receiving by the reader (220) batch data updates transmitted from the application residing on the mobile device.

In one aspect, the executable program instructions in memory further configure the microcontroller to perform the steps of: receiving by the reader (220) a request from the mobile device to transmit result data stored in memory to the mobile device; and transmitting the result data from the reader (220) to the mobile device.

In one aspect, the executable program instructions in memory further configure the microcontroller to perform the steps of: scanning by the first optical reader the first machine-readable optical code (212) and simultaneously scanning by the second optical reader the second machine-readable optical code (210) during insertion of the test cartridge (2) into the reader (220); reconstructing the timing data captured by the first optical reader using reference timing data stored in the memory to provide calibration data; interpreting the batch identifier captured by the second optical reader using the calibration data; retrieving the batch data associated with the test cartridge (2) from memory based on the batch identifier; and performing a test on the test cartridge (2) in accordance with the retrieved batch data.

In one aspect, the executable program instructions in memory further configure the microcontroller to perform the steps of: scanning by the first or the second optical reader the cartridge entry port (192) when the test cartridge (2) is removed from the reader (220); comparing features from an image of the cartridge entry port (192) stored in memory with features in the scanned image of the cartridge entry port (192); and if a feature is present in the stored image of the cartridge entry port (192) and in the scanned image of the cartridge entry port (192), notifying the user of an obstruction on the lens (183); and if a feature is present in only the scanned image of the cartridge entry port (192) and not in the stored image of the cartridge entry port (192), notifying the user to clean the lens (183).

After the comparison of the scanned image of the cartridge entry port and the stored image of the cartridge entry port, there are only two possible outcomes: (a) the reader detects dirt, debris, etc. (a feature) on the lens (due to differences between the two images) and informs the user to clean the lens; or (b) the reader does not detect any dirt, debris, etc. (a feature) on the lens (no message to user). When the stored image of the cartridge entry port is initially recorded (during calibration), the scan will have other elements recorded, such as the details of the spring on the bottom of the empty cartridge port. This image is saved as a reference in the reader memory. When the reader is being used, and after a cartridge is pulled out of the cartridge port, the reader will take a further scan (scanned image of cartridge entry port) and compare it with the scan already stored in its memory. It should see the same elements (spring, etc) as the stored image. If there are any additional elements or features (i.e., resulting from dust/particles on the lens) on the scanned image, it can be sufficiently different from the stored image that the reader's algorithm will pick it up as a dirty lens and will inform the user to clean it.

In one aspect, the executable program instructions in memory further configure the microcontroller to calibrate the reader (220) during manufacture by performing the steps of: setting a baseline sensor exposure time for the reader (220) using a first standard; and performing a scale optimization of the reader (220) using a second standard.

In one aspect, the first standard comprises a LF test strip and the second standard comprises a greyscale cartridge with an industry standard reflectance value.

In one aspect, there is provided a system comprising: the device (1) of any of the preceding claims; and a cloud database for storing batch data obtained during manufacture of a batch of the test cartridges (2); and an application associated with the reader (220) downloadable to a mobile user device, wherein the application is configured to receive batch data transmitted from the cloud database and result data transmitted by the reader (220) and to transmit batch data to the reader (220).

In one aspect, batch data obtained during manufacture of a batch of the test cartridges (2) is uploaded to the cloud database.

In one aspect, the application is further configured to send result data to the cloud database.

In one embodiment, the material of construction is suitably a durable yet rigid material, for example polypropylene, polyethylene (PE), polyethylene terephthalate copolymer (PETG), amorphous polyethylene terephthalate (APET), high impact polystyrene (HIPS), polycarbonate (PC), acrylonitrile butadiene styrene (ABS), polycarbonate (PC)-acrylonitrile butadiene styrene alloys, or combinations thereof.

The inventors present a pocket-sized, easy to use POC device, including a method for batch-to-batch calibration, that overcomes at least one of the issues mentioned above by removing the need for a user to undertake a specific calibration step by integrating a seamless calibration process through integration of barcode technology and analyte detection using a single linear sensor array combined with cloud-based data storage in a pocket-sized form factor. The use of all the combined elements of the POC device of the claimed invention enables hands-off calibration for the user. This enables accurate lot-to-lot performance without the user having to manually calibrate the instrument to every batch. All the calibration is done in the background as long as the user allows permissions for downloading data in the background.

In one aspect, the sensor is a linear sensor array.

The electronic reader may be an optical based system which measures reflected light, a camera system, or a fluorescent system. Preferably, the electronic reader is an optical based system. Ideally, the electronic reader is an optical based system using linear sensor array technology.

In one aspect, a green light source is preferred to specifically detect reflected light from red test and control lines that develop on the test strip.

In one embodiment, the sample collection chamber, and optionally the dilution chamber, is coated with an anticoagulant. The anticoagulant is selected from Ethylenediaminetetraacetic acid (EDTA), potassium EDTA, sodium EDTA, lithium EDTA, sodium fluoride, sodium oxalate, potassium oxalate, ammonium oxalate, sodium citrate, acid citrate dextrose, citrate phosphate dextrose, citrate phosphate dextrose adenine, lithium heparin, sodium heparin.

In one embodiment, the material of construction is suitably a durable yet rigid material, for example polypropylene, polyethylene (PE), polyethylene terephthalate copolymer (PETG), amorphous polyethylene terephthalate (APET), high impact polystyrene (HIPS), polycarbonate (PC), acrylonitrile butadiene styrene (ABS), polycarbonate (PC)-acrylonitrile butadiene styrene alloys, or combinations thereof.

In one embodiment, the information can be transmitted to a remote device over a wireless communication means for display on the remote device. In one embodiment, the remote device is a mobile phone device or electronic tablet device.

There is also provided a computer program comprising program instructions for causing a computer program to carry out the above method which may be embodied on a record medium, carrier signal or read-only memory.

The components of the device can be packaged together in a kit, or separately in a kit form. The device is suitable for reuse or suitable for a single use. The test cartridge is suitable for reuse or suitable for a single use. When being reused, the cartridge may be reused by replacing the test strip therein. The sample collection member and dilution chamber can be used once or reused following sterilisation. Typically, the collection member and dilution chamber will be pre-sterilised for single use only.

Definitions

In the specification, the term "sample conduit" should be understood to mean a member through which a sample is collected from a patient via, for example, a vacutainer holder, and through which the sample is delivered to either the dilution chamber or the test cartridge.

In the specification, the term "health event" should be understood to mean an event affecting the health status of an individual or patient, for example, an infection, a heart condition, a stroke, and the like.

In the specification, the term "snap(s)" or "snap-fit" should be understood to mean, as per the industry standard ("The First Snap-Fit Handbook", 1st Edition, (P. Bonenberger) (2000)) a mechanical joint system where part-to-part attachment is accomplished with locating and locking features (constraint features) that are homogenous with one or the other of the components being joined. Joining requires the (flexible) locking features to move aside for engagement with the mating part, followed by return of the locking feature toward its original position to accomplish the interference required to latch the components together. Locator features, the second type of constraint feature, are inflexible, providing strength and stability in the attachment. Enhancements complete the snap-fit system, adding robustness and user-friendliness to the attachment. The commonest form of snaps are annular (circular connectors), cantilever (hook and recess), and torsional (a latch is attached to a torsion bar or shaft). Annular snaps or annular press-fit snaps are used to create an interference fit between two parts in which one part is forced under pressure into a slightly smaller aperture in the other. Snap fits are commonly used as an assembly method for injection molded parts. The snaps are molded into the product, so additional parts are not needed to join them together. Additionally, if designed correctly, they can be disassembled and reassembled several times without any problems. A snap fit can either be designed as a permanent snap or a multiple snap. Permanent fits are used in disposable parts that are never meant to be disassembled. Multiple snaps are used in most designs where disassembly for service is expected.

In the specification, the term "patient" should be understood to mean any animal or mammal that requires monitoring to assess their health and well-being. For example, the patient can be selected from a human, a non-human mammal (ape, gorilla, chimpanzee, monkey, cetacean), domesticated livestock (porcine, equine, bovine, sheep) or any ruminant mammal, pets (dogs, cats, birds etc.), animals and mammals typically kept in a zoo or wildlife park (lion, tiger, elephant, rhino, wolf, sealions, seals, etc.).

In the specification, the term "Bluetooth®" should be understood to mean a wireless technology standard used for exchanging data between fixed and mobile devices over short distances using short-wavelength UHF radio waves in the industrial, scientific and medical radio bands, from 2.402 to 2.480 GHz, and building personal area networks (PANs).

In the specification, the term "Wi-Fi™" or "WiFi™" should be understood to a family of wireless networking technologies, which are commonly used for local area networking of devices and Internet access. Wi-Fi™ most commonly uses the 2.4 gigahertz (120 mm) UHF and 5 gigahertz (60 mm) SHF ISM radio bands; these bands are subdivided into multiple channels.

In the specification, the term "reader value scale optimization" should be understood to mean a reader value is taken every time the reader captures a scan. Every time a scan is made, the reader obtains a raw result from sensor, and then converts it into 'scaled signal' using four pieces of information:

The baseline data (in patent called baseline);

The grey signal (scan of 18% reflectance strip);

The raw scan (the scan of the inserted cartridge); and

The known reflectance value (0.18 for 18%).

The above information is used to translate the RAW values into SCALED values (for every pixel) using a scaling algorithm. In short, the greyscale cartridge is used to capture a trace which is saved into the reader memory. This trace (along with the known reflectance value) is then used by the reader to scale the result every time a reading is taken. So, one might say that the actual "reader value scale optimization" does not happen during calibration, but instead happens after a reading is taken. Calibration only captures a reference signal with known reflectance and saves it into memory. This signal is then used in post-processing stage, after a reading is taken, to convert raw values into scaled values.

In the specification, the term "reflectance value" should be understood to mean the amount of reflectance in visible light. Middle grey was defined as the geometric mean intensity between a white and a black intensity that are in a ratio of 60:1. That is equivalent to 12.9% of the white intensity. Typically, middle grey is defined as 18% reflectance in visible light. This grey reflects exactly $1/5^{th}$ the number of photons per square unit as compared to a reference white of 90% reflectance. The reflective values could range from 1 to 99%. Selection of this value depends on the operating range of the system. For example, if a system operates within the range of 0-60%, then a scale in the 20%-40% range would be best selected.

In the specification, the term "decoding algorithm" should be understood to mean decoding a scan of an unknown barcode which moves underneath a single photodiode. To decode a scan of the unknown barcode, the speed of the movement (insertion speed when talking about a barcode placed on a cartridge) must be known, unless it is assumed to be constant throughout the entire scan. This is because the width of the barcode lines is directly proportional to the barcode velocity when the photodiode output is read at constant intervals. When both the input (apparent image of the barcode resulting from the scan) and the output (the actual dimensions of the barcode) are known, the insertion speed can be obtained as follows:

The timing data representing the cartridge insertion speed can be obtained by comparing the digitized scan of the first machine-readable optical code (apparent dimensions of the real barcode resulting from the movement of the barcode underneath the sensor with unknown speed) with the pre-programmed knowledge of the real physical dimensions (line width and line placement) of the barcode. The now known insertion speed derived from the timing data can be used to decode the second machine-readable optical code, whose real dimensions are unknown to the reader.

This dual-barcode system allows for reliable reading of barcodes even when the insertion speed is not constant, which can be a case when the cartridge is inserted manually by the user.

In the specification, the term "1D 2 of 5 interleaved" should be understood to describe an industry standard type of barcode. There are different types of configurations used to create the markings of a barcode that will determine how much information can be "decoded" by the reader of the claimed invention. In this case, a 1D 2 of 5 type of barcode system is being used.

In the specification, the term "at angle" with respect to the angle of the light emitted from the light source is directed to the test strip at an angle via sloped sides should be understood to be that as the light from the light source is traveling at a non-perpendicular angle relative to the cartridge and the test strip, the cartridge window has sloping (angled) walls in order to avoid the side-walls casting shadow onto the strip. Ideally, the walls of the cartridge should be sloped at a lesser angle than the angle of the incidence of the light coming from the light source. This ensures that the light is 'guided' by the wall slope and does not cast shadow onto the strip. When talking about the angle of the slope here, 90 degrees=vertical wall, 0 degrees=no wall (flat surface). Therefore, lesser angle means further from the vertical wall. Angle of incidence is the angle between the light ray and the line perpendicular to the surface. Due to the nature of the light source, where the light is not perfectly collimated and some scattering occurs, the slope of the cartridge walls is not critical and does not need to be perfect: a wide range of angles will still work, and it is assumed that the lesser angles provide better performance.

In the specification, the term "rod lens" should be understood to mean a cylindrical lens which has the geometrical form of a cylinder, while the two flat end surfaces may be ground.

In the specification, the term "collimator" should be understood to mean a device which narrows a beam of particles or waves. To narrow can mean either to cause the directions of motion to become more aligned in a specific direction (i.e., make collimated light or parallel rays), or to cause the spatial cross section of the beam to become smaller (beam limiting device).

BRIEF DESCRIPTION OF THE DRAWINGS

The invention will be more clearly understood from the following description of an embodiment thereof, given by way of example only, with reference to the accompanying drawings, in which: —

DETAILED DESCRIPTION OF THE DRAWINGS

The present invention describes a handheld, portable and, optionally, an integrated point-of-care (POC) device, which does not require the use of a benchtop to operate and that is suitable for use in point-of-care, quarantine and field use, as well as for general monitoring and screening of patient health and/or their response to treatment. The device described herein is easy to use and performs and manages the necessary steps in a single integrated housing, reducing the input required by the professional or the home user, and reducing the likelihood of introducing error.

Figure 1:
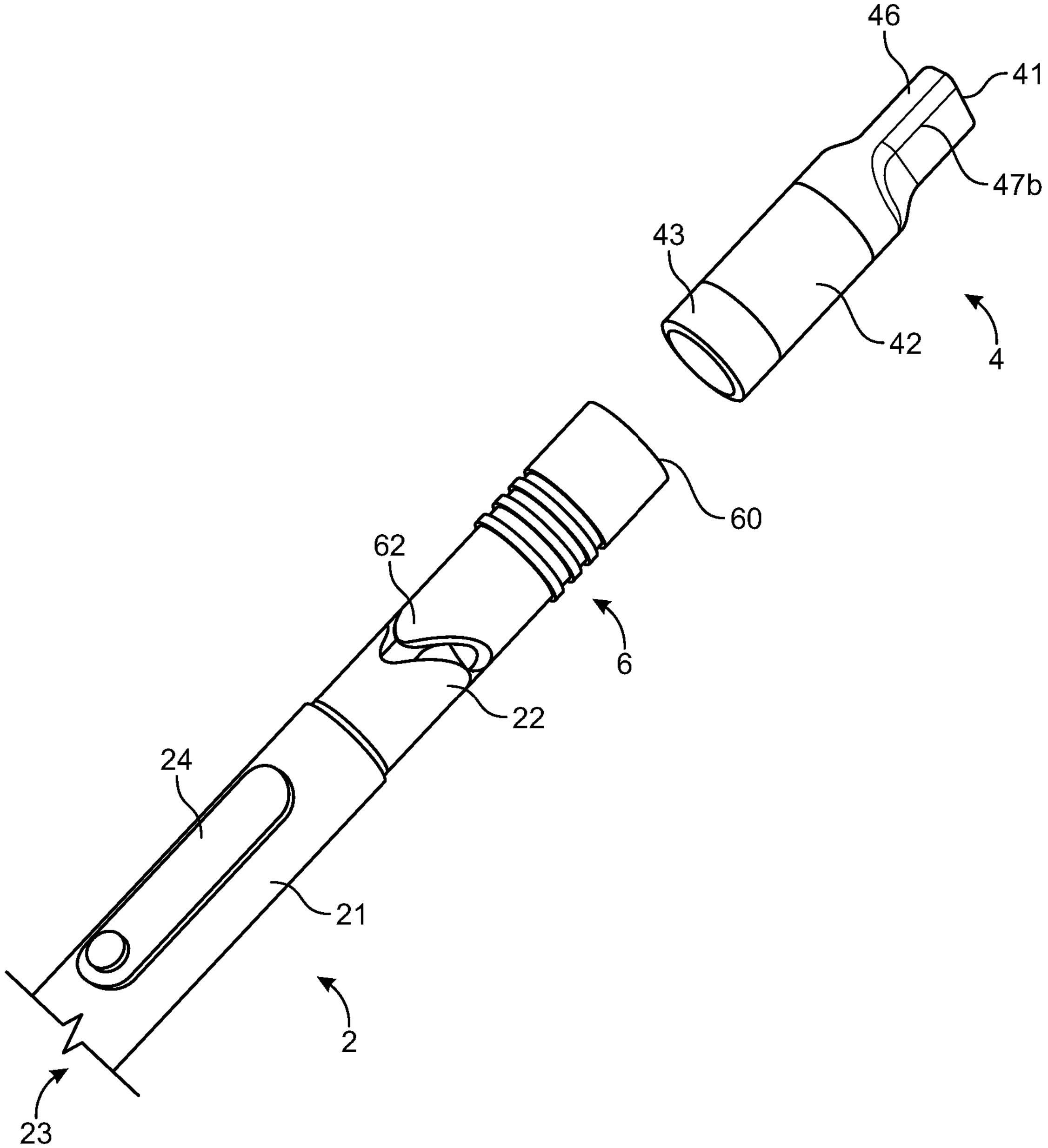
FIG. 1 illustrates an exploded view of a device of the claimed invention.
Figure 8A:
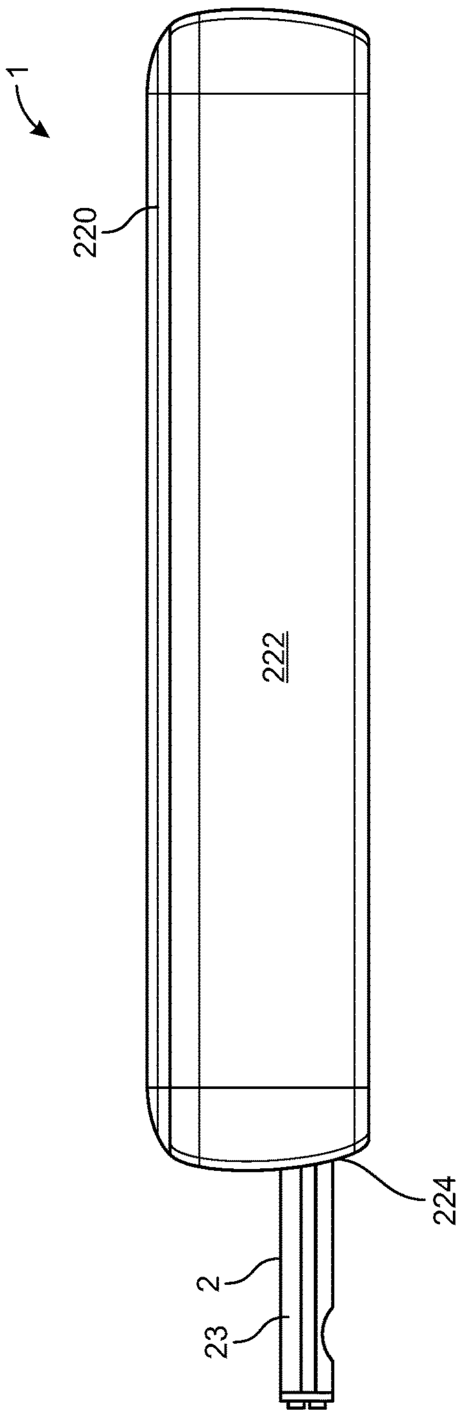
FIG. 8 illustrates (A) a side profile view of the cartridge inserted into the reader of the claimed invention and (B) is a cross-section view of (A).

Referring now to the figures, where FIG. 1 illustrates a general embodiment of a POC device of the present invention. Specifically, FIG. 1 illustrates an exploded view of a POC device of the claimed invention, and is generally referred to by reference numeral 1. The POC device 1 comprises a test cartridge 2 and a sample collection member 4, which are separated by a dilution member 6 (collectively called components). The dilution member 6 is an optional feature which is adapted to engage with both the test cartridge 2 and the sample collection member 4. The dilution member 6 generally holds a specific volume of diluent for the sample collected prior to sample testing. A reader 220, as shown in FIG. 8(A), is an integral part of the device 1, and is discussed in more detail below.

The sample collection member 4 comprises a distal end 41 configured to be gripped by a user, a sample chamber 42 configured to accept a volume of sample and a proximal end 43 configured to engage with either one of a vacutainer holder 10, the test cartridge 2 or the dilution member 6. In the illustrated embodiment, the distal end 41 comprises a gripping member 46 having a depression 47*a*,47*b* on opposite sides of the distal end 41.

Figure 2A:
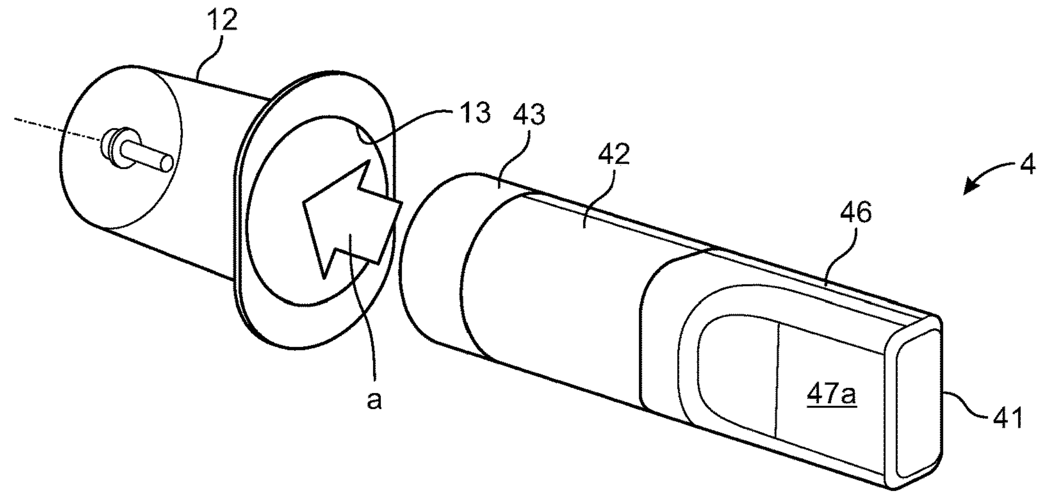
FIGS. 2A-C illustrate a sample collection member of the device of FIG. 1 collecting a sample.
Figure 2B:
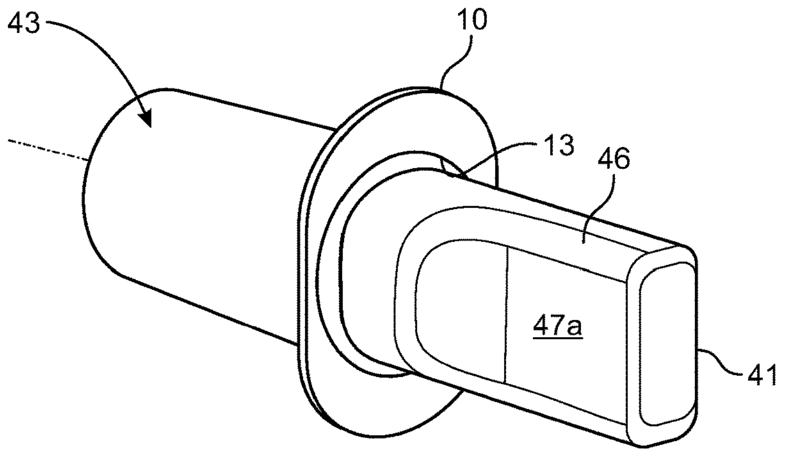
Figure 2C:
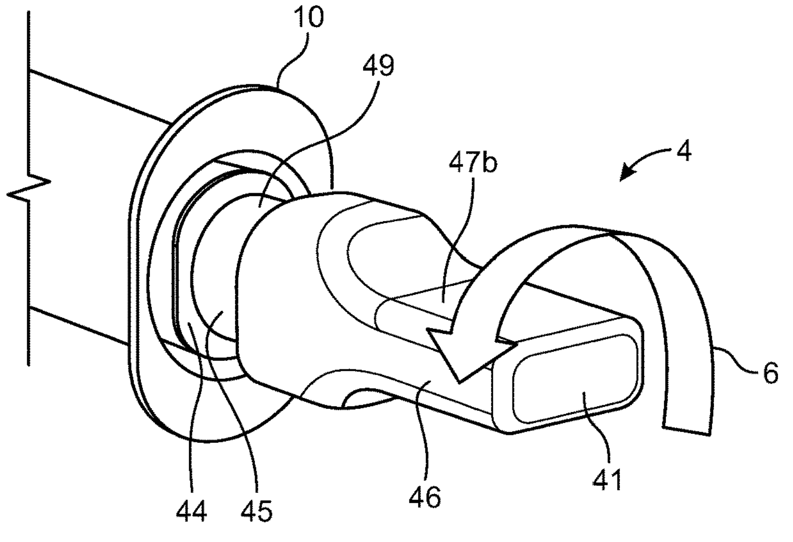

When collecting a sample, as illustrated in FIGS. 2A-C, the sample collection member 4 engages with the vacutainer holder 10 commonly used by medical professionals when taking samples from the body. The proximal end 43 of the sample collection member 4 is inserted within a chamber 13 of the vacutainer holder 10 and engages with a sample delivery member 12 (see arrow a in FIG. 2A). The sample delivery member 12 is generally a needle or a sharp capillary tube, one end of which is in a patient's vein (for blood) or spinal cord (for cerebrospinal fluid) and the other end is within the chamber 13. The sample delivery member 12 engages with the distal end 43 of the sample collection member 4 (see FIG. 2B). Typically, the proximal end 43 of the sample collection member 4 comprises a sample conduit 48 (see FIG. 3A). Typically, the sample conduit 48 is a female connector adapted to receive the sample delivery member 12 of the vacutainer holder 10. Alternatively, the sample conduit is a self-sealing rubber seal which permits insertion and removal of the sample delivery member 12 from the sample chamber 42 without loss of sample from the sample collection member 4.

Typically, the dilution member 6 comprises a distal end 60 and a proximal end 62, distal and proximal the test cartridge 2, respectively. The dilution member 6 is further defined by a mixing chamber 63, where the sample is diluted with a buffer or other suitable solution. The test cartridge 2 typically comprises a housing 21, a proximal end 22 and a distal end 23. The test cartridge 2 can also have a display panel 24.

In order to obtain a metered sample from the patient, the user grips the depressions 47*a*,47*b* of the gripping member 46 and twists the distal end 41 of the collection member 4 in a counter-clockwise movement (up to 90°), as per the direction of arrow b (see FIG. 2C). This movement releases the distal end 41 from the sample chamber 42. The distal end 41 and the sample chamber 42 are engaged by a typical male/female connection. Housed within the distal end 41 is an engagement member 45. The engagement member 45 is typically a threaded bore with a corresponding engagement (threaded) member 44 on the sample chamber 42, or else the engagement member 45 is a luer lock mechanism. The release of the engagement of the distal end 41 with the sample chamber 42 permits movement of the distal end 41 away from the sample chamber 42. The distal end 41 is shown to further comprise a retractable piston 49 which acts to pull sample in from the vacutainer holder 10 into the sample chamber 42 once the distal end 41 is disengaged from the sample chamber 42. The retraction of the piston 49 and the vacuum seal formed between the proximal end 43 of the collection member 41 and the vacutainer holder 10 causes the sample to be collected via the vacutainer holder 10. This vacuum seal causes a metered volume of sample to be collected from the patient via the sample delivery member 12 and stored within the sample chamber 42. The volume of sample collected is directly correlated to the number of degrees of rotation of the distal end 41. The rotation of the distal end 41 provides both visual and tactile feedback to the user.

When the sample collection member 4 is removed from the vacutainer holder 10, having received its metered volume of sample fluid, the user has two options: (i) deliver the sample directly to the test cartridge 2 or (ii) connect the sample collection member 2 to the dilution member 6 and then connect to the test cartridge 2. In the embodiment illustrated in FIGS. 4 to 7, option (ii) is shown. However, the means by which the sample is directly delivered to the test cartridge is identical whether option (i) or option (ii) is chosen.

Figure 3A:
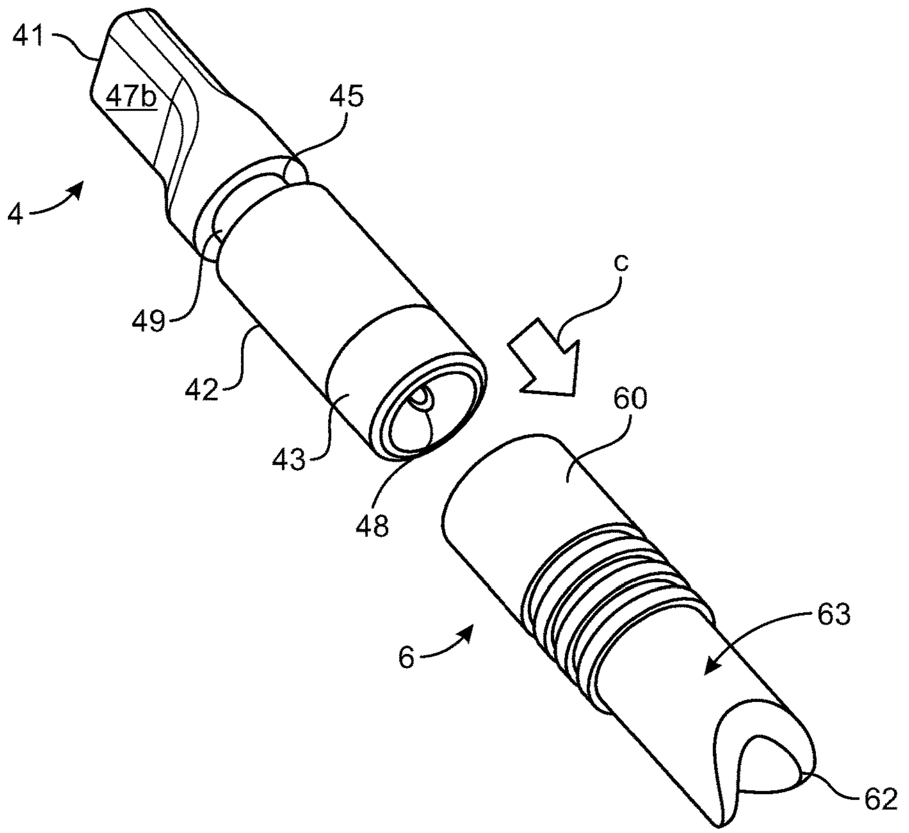
FIGS. 3A and B illustrate the sample collection member engaging with an intermediate dilution chamber of the device of FIG. 1.
Figure 3B:
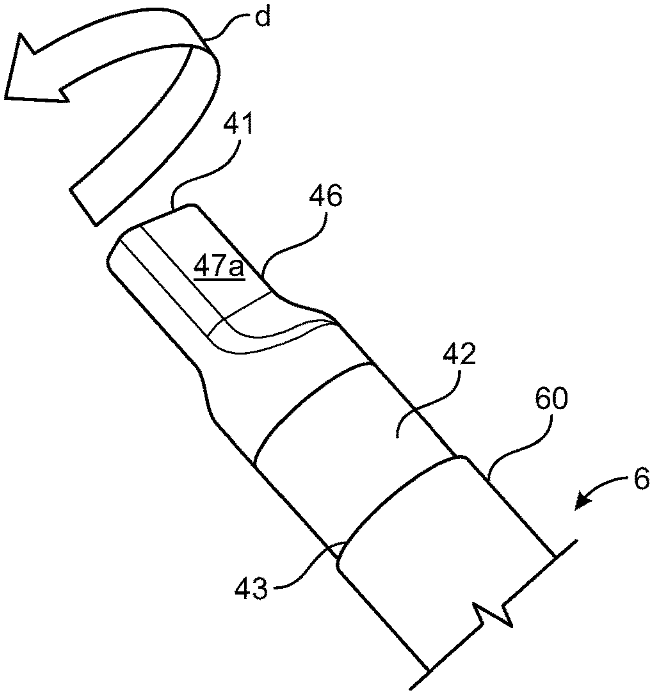

In use, as illustrated in FIGS. 3A and B, the proximal end 43 of the collection member 4 is inserted into a distal end 60 of the dilution member 6. The outer diameter of the collection member 4 is narrower than an internal diameter of the distal end 60 of the dilution chamber 60. When the sample collection member 4 is pushed into the distal end 60 (see arrow c), a friction fit is formed between collection member 4 and the sample member 6. The user then twists the distal end 41 of the collection member 4 in a clockwise fashion around 90°, as indicated by arrow d. The twisting causes the distal end 41 to reengage with the sample chamber 42. This reengagement causes the sample to enter into the mixing chamber 63 of the dilution member 6. A more detailed explanation of how the sample enters the dilution member 6 is described for FIG. 5.

Figure 4A:
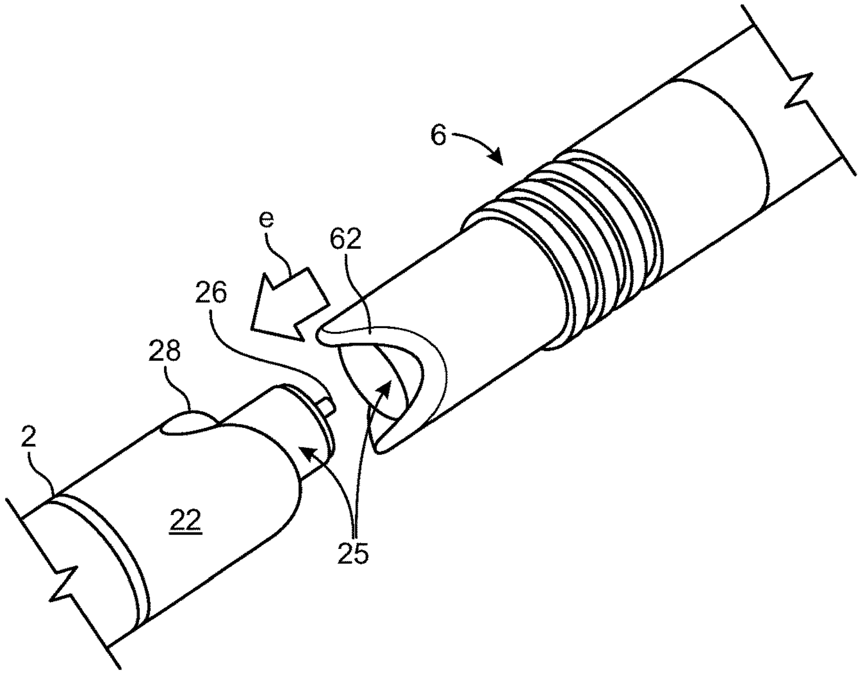
FIGS. 4A-C illustrate the intermediate dilution chamber engaging with a test cartridge of the device of FIG. 1.

Once the sample collection member 4 and the dilution member 6 are engaged, the proximal end 62 of the dilution member 6 engages with the proximal end 22 of the test cartridge 2. As shown in FIG. 4A, the proximal end 62 and the proximal end 22 are adapted to engage with one another forming a secure fit. The proximal end 62 comprises a receptacle 64 for receiving a sample receiving member 25. The sample receiving member 25 extends outward from the proximal end 22 of the test cartridge 2. The sample receiving member 25 further comprises a collection chamber 26, which protrudes outwards from the receiving member 25 and is adapted to engage with a dispensing chamber 68 of the dilution member 6. The dispensing chamber 68 is fixed to the internal walls of the mixing chamber 63 (see FIG. 5 and FIG. 6). The dispensing chamber 68 is a hollow, open-sided channel 69 within which can be found a plug 70 that is maintained within the confines of the dispensing chamber 68 by an interference fit.

Figure 4B:
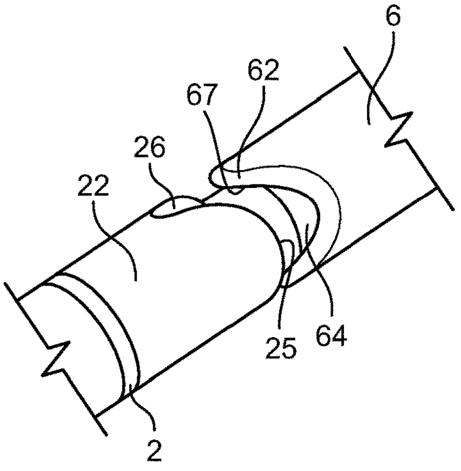
Figure 4C:
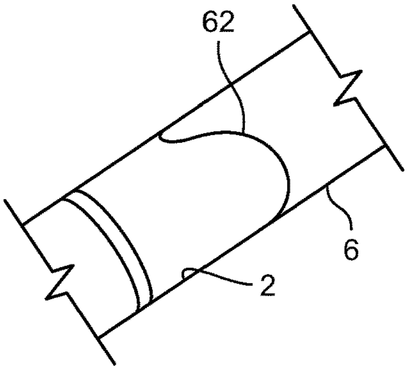

The inner diameter 67 of the receptacle 64 is generally smaller than the outer diameter 25*a* of the sample receiving member 25. This arrangement permits the receptacle 64 to engage with the receiving member 25. The proximal ends 22,62 each further comprise a lip 28,66 configured to engage and secure the components 2, 4, 6 together. When the components 2, 4, 6 of the device 1 are pushed together (as per arrow e), as illustrated in FIGS. 4B and C, the device 1 is an integrated, sealed POC device.

Figure 5:
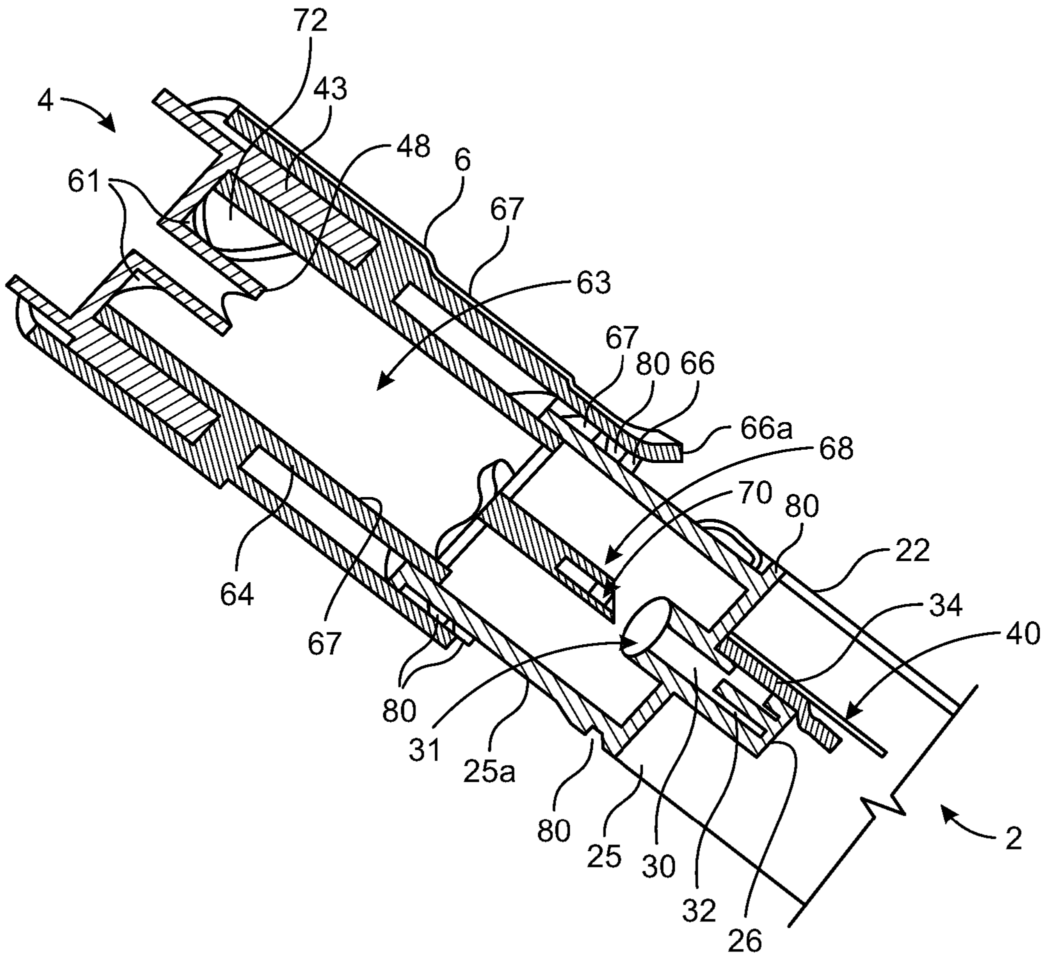
FIG. 5 is a cross-section of the area of the device of FIG. 1 at the junction where the sample collection member, the intermediate dilution chamber and the test cartridge are connected together.
Figure 6:
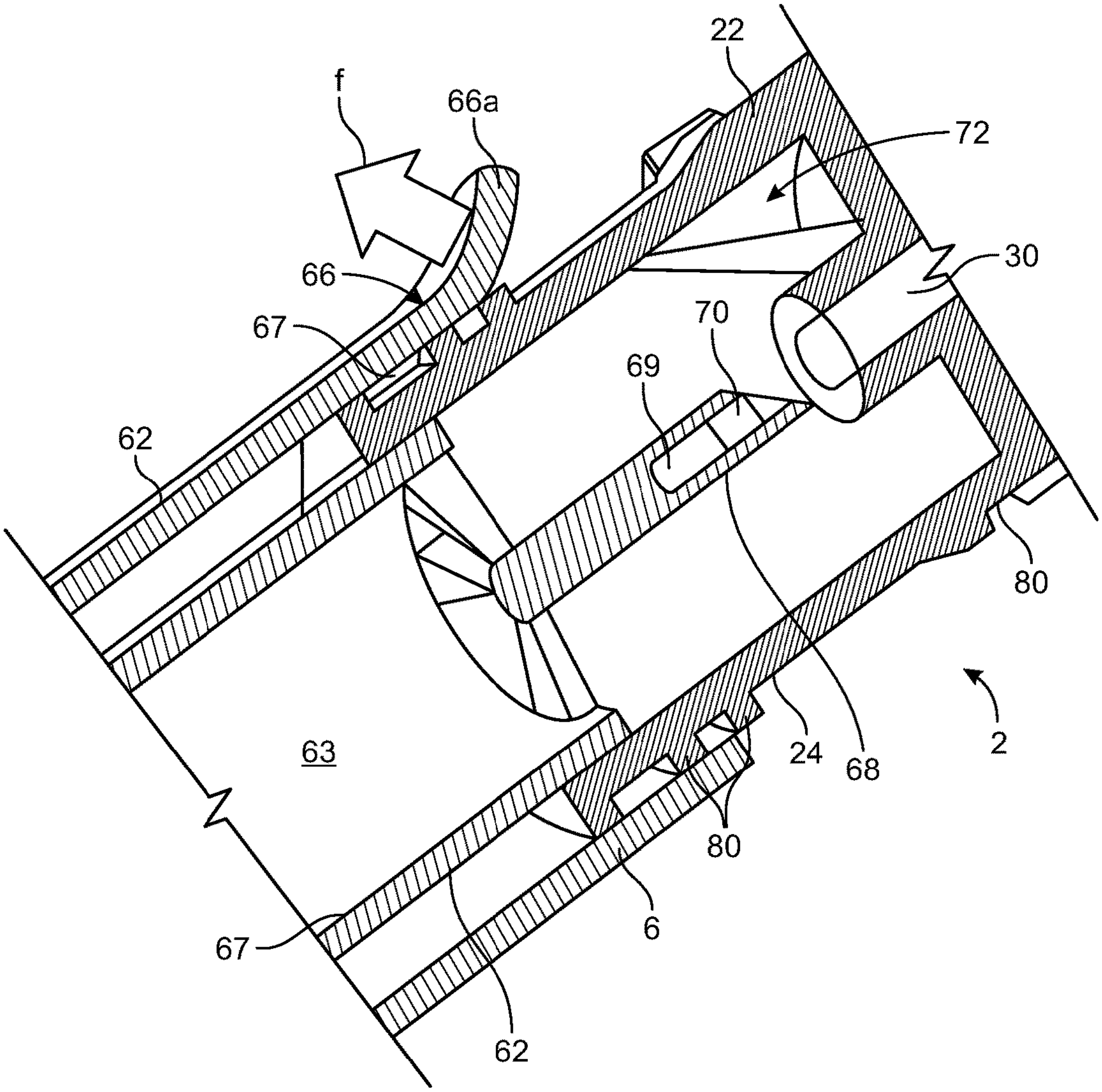
FIG. 6 illustrates a cross-section of the device of FIG. 1 showing the interaction of the dilution chamber and the test cartridge prior to sample delivery to the test cartridge.

As shown in FIG. 5, the sample collection member 4 is engaged with the dilution member 6, which is engaged with the test cartridge 2. The three components lock together using snap-fit 80 fittings. The snap-fits 80 are found on the circumference of the ends 22, 23, 41, 43, 60, 62. The collection chamber 26 of test cartridge 2 further comprises a sealed aperture 31, a sample holding area 30 within which is a baton 32 protruding upwards towards the sealed aperture 31 and a window 34. The window 34 provides access to the test strip 40 for the sample being tested.

The proximal end 62 further comprises a tab 66 with a push/pull member 66*a*. The tab 66 has a lock and release tab 67 that is configured to engage with snap-fits 80 on the circumference of the proximal end 22. The tab 66 is configured to permit the user to move the dilution chamber 6 towards the test cartridge 2. The tab 66 is shown in a locked position which prevents premature puncturing of the sealed aperture 31 leading to the sample collection chamber 26. Pulling the tab 66 in the direction of arrow f releases the snap-fits 80 of the of dilution member 6 and test cartridge 2, allowing the components to move freely.

In use, when the sample collection member 4 has collected its sample, the proximal end 43 is engaged with the distal end 60 of the dilution member 6. By rotating the distal end 41 of the sample collection member 4 in a clockwise direction, the piston 49 re-enters into the sample chamber 42 and forces the sample conduit 48 to penetrate a seal 61 at the distal end 60 of the dilution member 6. The penetration of the sample conduit 48 causes the sample to enter into the mixing chamber 63 of the dilution member 6. The device 1 is then shaken or turned upside down a number of times to permit mixing of the sample with a dilution buffer present in the mixing chamber. Alternatively, a floating widget or floating member may be placed within the mixing chamber to aid in mixing the sample with dilution buffer. As the volume of sample and volume of dilution buffer is predetermined, an air bubble 72 is constantly present within the mixing chamber 63 when the sample is delivered. Air is lighter than the liquid, so the air bubble 72 will always sit on top of the liquid, no matter what orientation the device 1 is held in. The volume of the air bubble 72 is known, so the geometry of the mixing chamber 63 has been designed such that the air bubble 72 does not interfere with the dispensing chamber 68. The air bubble 72 ensures that it will be possible to mix the sample and dilution buffer thoroughly when the device is shaken or agitated. By agitating the device 1, the dispensing chamber 68 is filled with a predetermined volume of diluted sample. When there is sample and dilution buffer present in the mixing chamber 63, the dispensing chamber 68 is always submerged with fluid, regardless of the device's orientation (see FIG. 5 and FIG. 6). Further, because of the ratio of air bubble to diluent and the geometry of the internal structure of the mixing chamber 63 ensure that the air bubble 72 is never in a position to interfere with the dispensing chamber 68. The dispensing chamber 68 is positioned centrally and air bubbles will always rise to the edge and away from the mixing chamber 68.

The device 1 is seen to be in an "inactive" mode, that is, where the sample and dilution buffer have been mixed together in the mixing chamber 63, but where the mixed sample has not yet been introduced to the test strip 40 in the test cartridge 2. It could also be stated that the device 1 is in an inactive mode following sample collection but prior to introducing the collected sample into the mixing chamber 63.

Figure 7A:
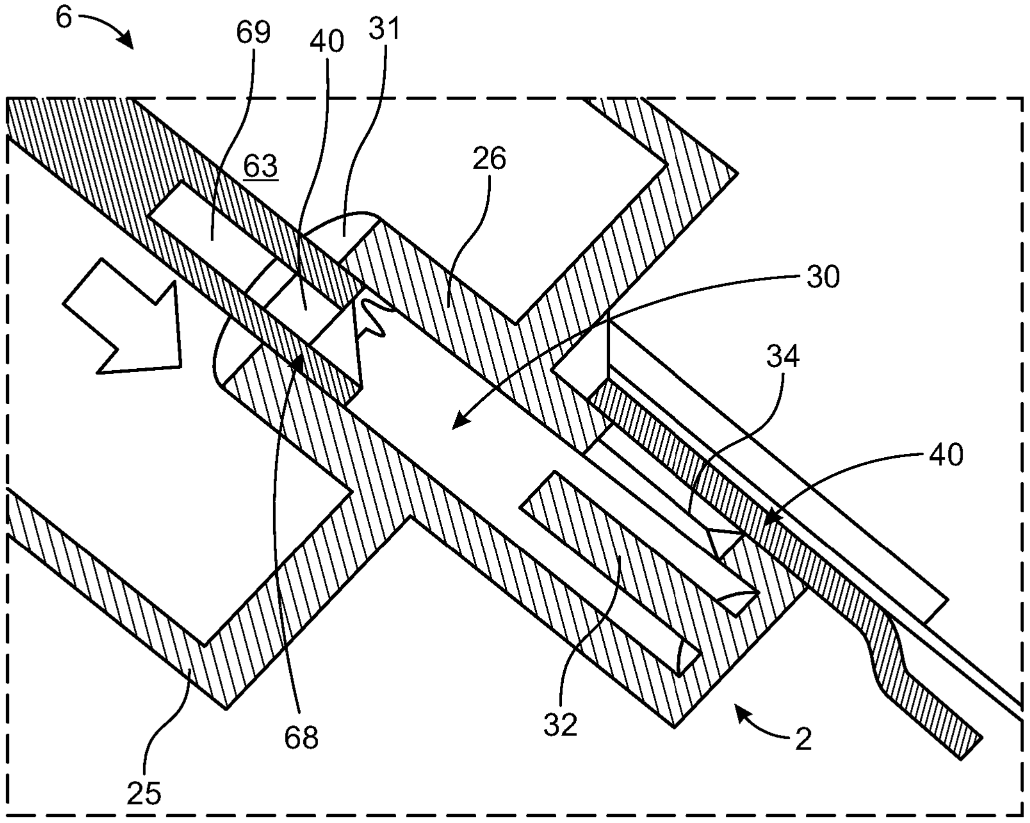
FIGS. 7A-C illustrates a cross-section of the device of FIG. 1 at the junction where the intermediate dilution chamber and the test cartridge are connected together and showing the delivery of sample from the dilution chamber to the test cartridge for testing.
Figure 7B:
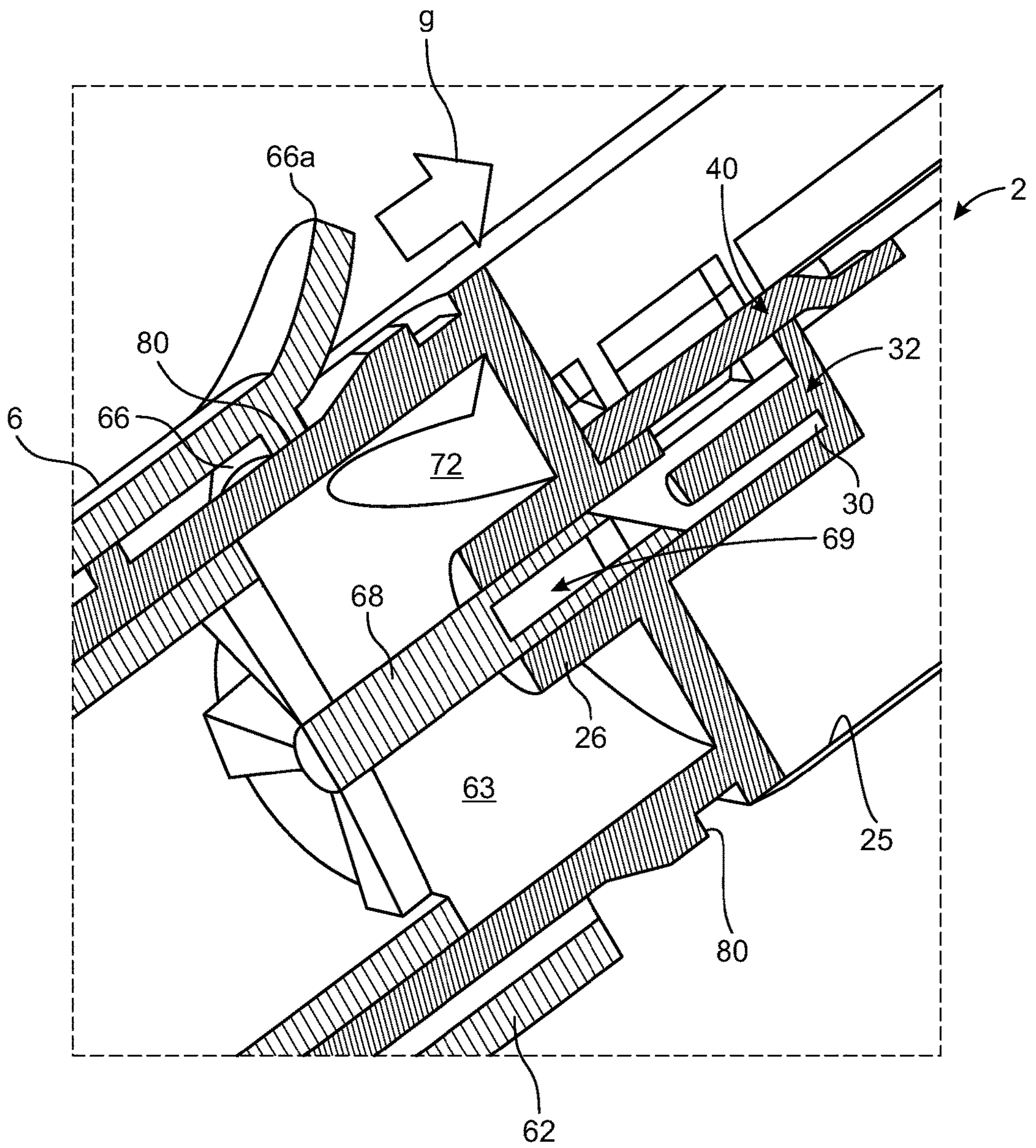
Figure 7C:
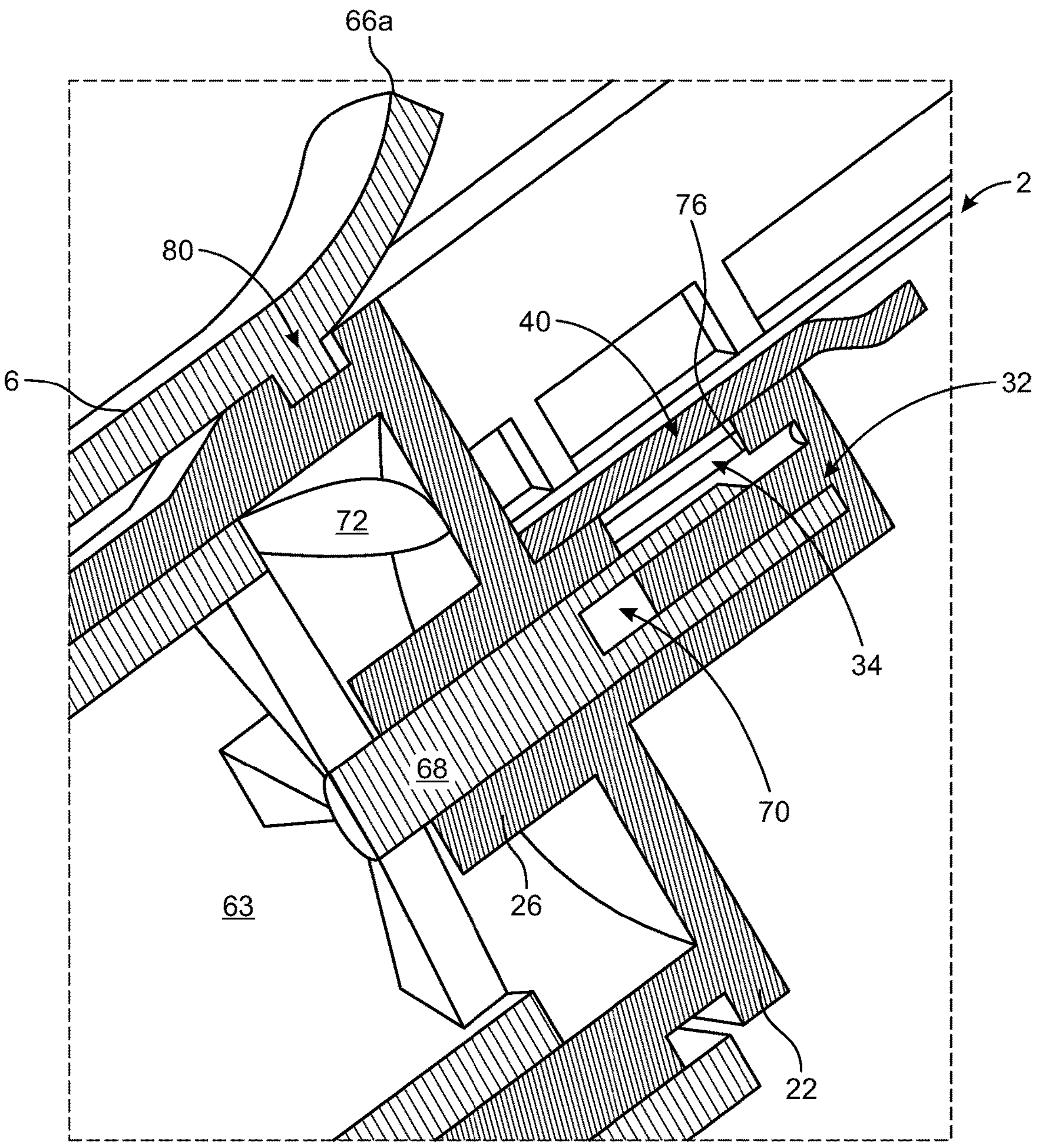

The details of how the various components of the device 1 fit together and deliver sample is outlined in FIGS. 7A-C. To activate the device 1, the tab 66 is pushed and pulled to release the release tab 67 from its corresponding snap-fit 80. The dilution chamber 6 is now free to move its proximal end 62 towards the proximal end 22 of the test cartridge 2. In doing so, the dispensing chamber 68 is moved forward (in the direction of arrow g) towards the sealed aperture 31 of the collection chamber 26. The movement of the dilution chamber 6 causes the dispensing chamber 68 to pierce the sealed aperture 31 (see FIG. 7A and FIG. 7B). The plug 70 prevents any sample from entering the collection chamber 26 by creating a barrier and prevents any excess sample from the mixing chamber 63 to enter the collection chamber 26. The plug 70 functions by having less resistance (in its position) than the force applied to it by the baton 32 when the tab 66 is pulled/pressed and the dispensing chamber 68 moves into the sample collection chamber 26.

As the dilution chamber 6 is pushed further into the sample receiving chamber 25 of the test cartridge 2, the baton 32 enters the confines of the channel 69 of the dispensing chamber 68. When the baton 32 comes into contact with the plug 70, the baton 32 pushes the plug 70 back up into the channel 69 of the dispensing chamber 68, displacing sample therein and forcing the sample into the window 34 above the test strip 40 where there is an air pocket 76. This second air pocket 76 is the only available pocket for sample to move into. The opposing open side of the collection chamber 26 is blocked off by the geometry of the collection chamber 26, thus blocking fluid exit on that side. The metered sample is now presented to the test strip 40 through the window 34.

One of the advantages of the plug 70 is that it also serves to protect the sample as it moves through the sealed aperture 31 and also ensures that all of the metered samples is expelled from the dilution chamber 6.

Figure 8B:
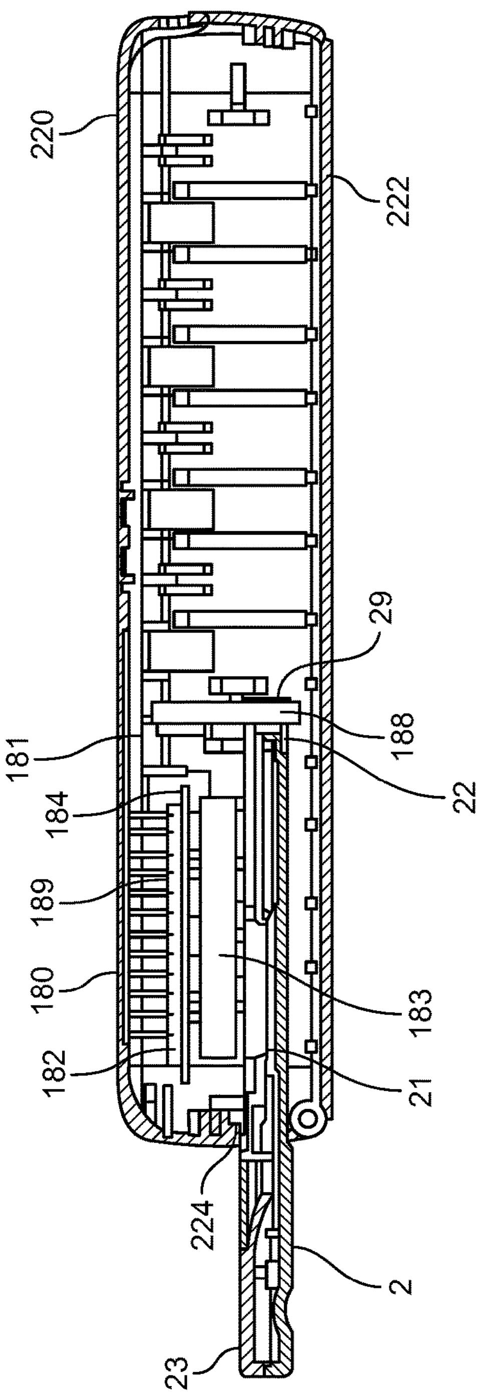
Figure 9:
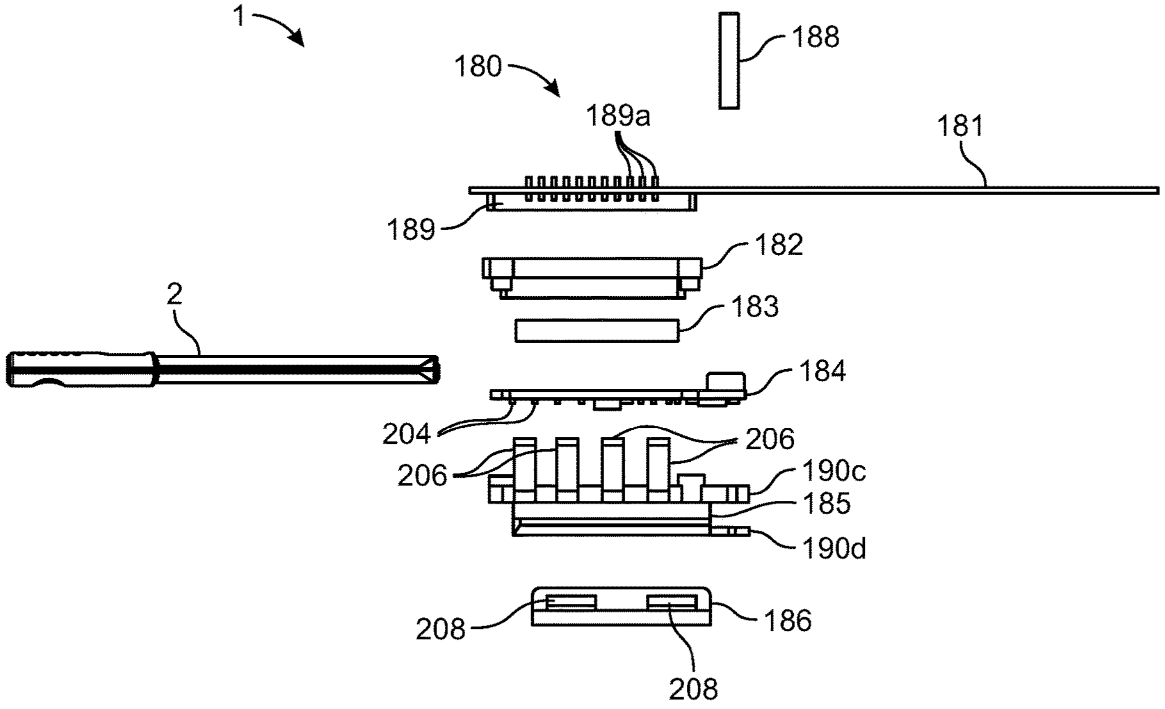
FIG. 9 illustrates an exploded view of a chassis stack of the device of the claimed invention, together with an alignment pin and a test cartridge of one aspect of the claimed invention.

FIG. 8(A) is a side view of the test cartridge 2 inserted into a reader 220 of the claimed invention, while FIG. 8(B) is a cross-sectional view of the former. The reader 220 comprises a casing 222 having a cartridge insertion port 224. The casing 222 houses an optical chassis stack 180. FIG. 9 illustrates an exploded view of the optical chassis stack 180 of the reader 220 of the claimed invention. The test cartridge 2, which is shown with a different shape to that depicted in FIG. 1 and FIG. 7, is present to illustrate scale. The optical chassis stack 180 comprises a first printed circuit board (PCB) 181, a lens holder 182, a lens 183, a second PCB 184, a chassis 185, a cartridge port 186 with springs 208, and a linear sensor array 189. The lens (183) is typically composed of a plurality of lenses forming a lens array or an array of lenses. The linear sensor array 189 further comprises a plurality of locating/connecting pins 189*a* that push through holes on the first PCB 181. The optical chassis stack 180 of the reader 220 defines a sensing system (the sensor 189, the lens holder 182, the lens 183, and the first and second PCBs 181,184), and determines the way that reflectance data from test cartridges 2 is captured. For example, in order for the linear sensor array 189 to capture reflectance data from the test cartridge 2, the elements of the optical stack 180 must be arranged in adequate physical positions in relation to the cartridge insertion port 224 into which the test cartridge 2 is inserted. The light emitted by a light source 204 (for example, a light-emitting diode (LED)) on the second PCB 184 must travel thought the optical stack 180 and bounce off the test strip 40 inside the cartridge 2 held by the spring 208 in the cartridge port 186. The reflected light must then travel up the optical stack 180 through the lens 183 held by the lens holder 182 to the linear sensor array 189 mounted on the first PCB 181. Therefore, the physical relationships between all the elements of the optical chassis stack 180 must accommodate the required light paths for the reflectance data to be captured. In order to ensure that the device 1 is reliable for use in a POC setting, the inventors have identified the arrangement of the linear sensor 189 relative to the lens 183 and the test strip 40, the position and the angle of the light source 204, and the geometry of the cartridge port 186 and the optical chassis stack 180 are integral to the performance of the reader 220.

In the illustrated example, the first PCB 181 is mounted with the linear sensor array 189 and the second PCB 184 comprises an aperture 202 (illustrated in FIG. 15) and the illuminating light source 204. The lens 183, is typically an array of flat-ended, gradient-index lens (a SELFOC lens) held in the chassis 185. The optical chassis stack 180 encompasses the sprung cartridge port 186 and accommodates the cartridge 2 (when inserted). The first and second PCBs 181,184 are assembled with the first PCB 181 on top and the second PCB 184 beneath, separated by the lens holder 182. The optical chassis stack 180 is held together using clips or snap-fits 206 on the chassis 185 and an alignment pin 188. The optical chassis stack 180 of the reader 220 allows for a significantly reduced device footprint, thus enabling the reader 220 to be pocket-sized.

Alignment of the cartridge 2 containing the LF test strip 40 is crucial for reliable and repeatable test performance. In the platform of the claimed invention, the alignment is by integration of the alignment pin 188 around which the main components are assembled. The alignment pin 188 also functions as a receiving feature for the cartridge 2 and acts as a positive positioning indicator for the user. This positive positioning indication from the alignment pin 188 informs the user that the cartridge 2 has been inserted into the reader 220 correctly. The alignment pin 188 travels down through a shaft 190 that continues down through the components of the optical chassis stack 180 from the first PCB 181 to the chassis 185. The shaft 190 is typically composed of three or four engagement means, namely, engagement means 190*a*, 190*b*, 190*c* and 190*d*. The first engagement means 190*a* is an aperture at the entrance to the shaft 190 on the first PCB 181; the second engagement means 190*b* is also an aperture located on the second PCB 184; while the third engagement means 190*c* and the fourth engagement means 190*d* are snap-fit elements located on the chassis 185 (see FIG. 10). The alignment pin 188 is inserted through the first engagement means 190*a* in the first PCB 181 that incorporates the linear sensor array 189; then it passes through the second engagement means 190*b* in the second PCB 184 which holds the illuminating light source 204; and then it passes through the third engagement means 190*c* in the chassis 185. In one aspect, as show in FIG. 15, the fourth engagement means 190*d* of the shaft 190 is not required. In one aspect, the alignment pin 188, which traverses the third engagement means 190*c* and which is part of the chassis 185, interacts with a snap-fit element 29 on the proximal end of the cartridge 22, that when engaged, produces both haptic and audible feedback to the user, indicating that the cartridge 2 has been inserted correctly. Once the cartridge 2 has been correctly inserted, the alignment pin 188 will maintain the correct position of the cartridge 2 by engaging with the snap-fit element 29 on the proximal end 22 of the cartridge 2 when the cartridge is inserted (see FIG. 11 and FIG. 13(B)). The alignment pin 188 is typically constructed form a durable material such as stainless steel, or other suitable metal and hard-wearing plastic materials.

Figure 15:
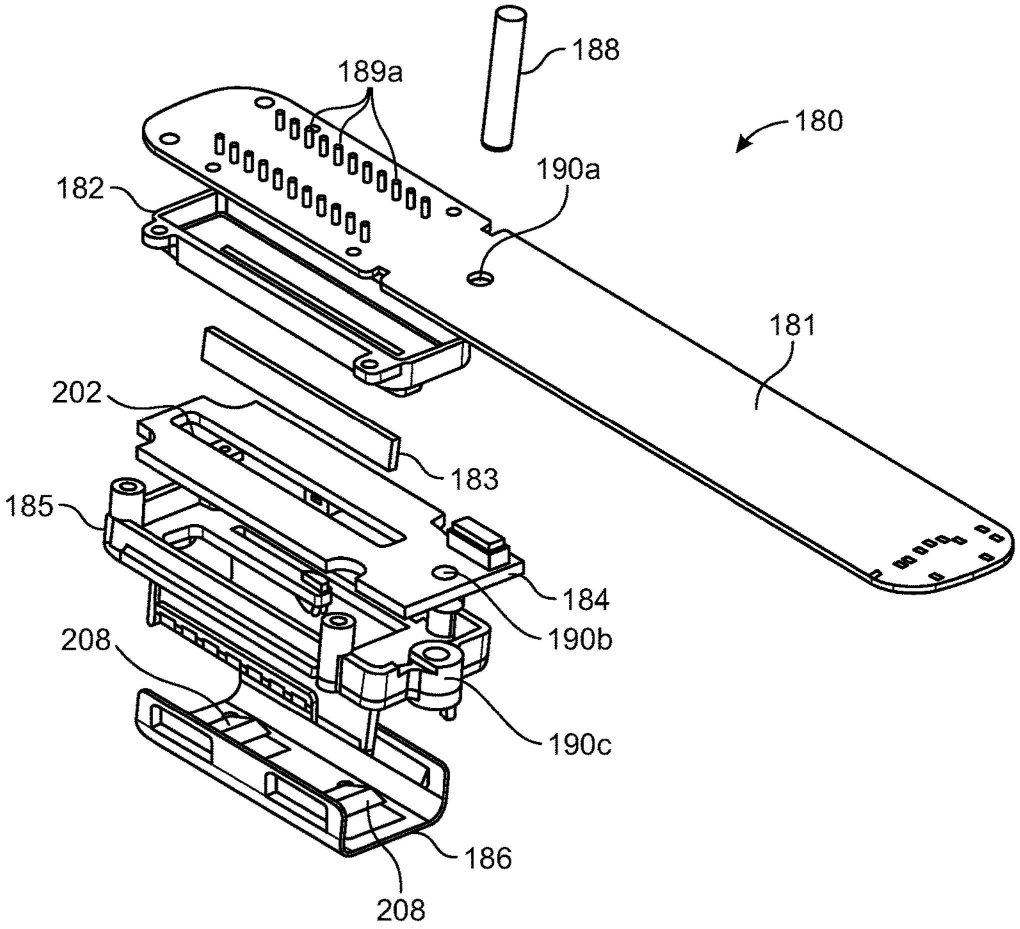
FIG. 15 illustrates an exploded, perspective view of the chassis stack of FIG. 9.

FIG. 15 also illustrates an embodiment where the snap-fits 206 are replaced with a male/female arrangement 199 and the fourth engagement means 190*d* is removed.

Other versions of the assembly may use other means to hold the assembly together, along with the alignment pin 188.

Figure 10:
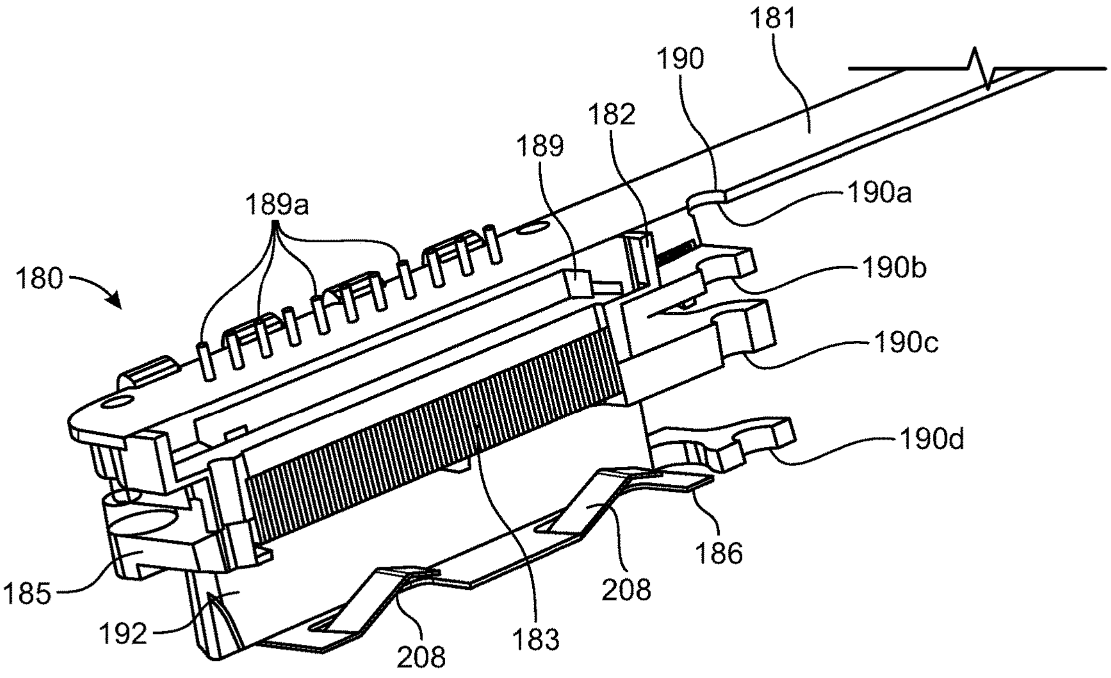
FIG. 10 illustrates a cross-sectional perspective view of the chassis stack of FIG. 8 with the alignment pin removed.
Figure 11:
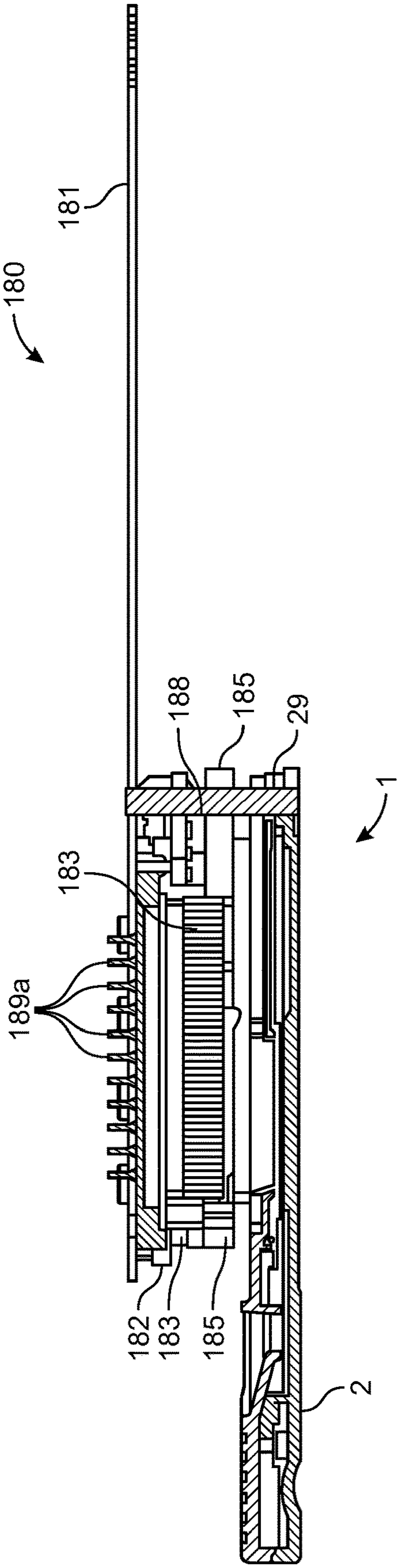
FIG. 11 illustrates a cross-sectional side view of the chassis stack of FIG. 8 and FIG. 9 with the alignment pin and the test cartridge in situ.

FIG. 10 and FIG. 11 illustrate a cross-sectional perspective view of the optical chassis stack 180 of FIG. 9. A cartridge entry port 192 is formed by combination of the chassis 185 and the cartridge port 186. The shaft 190 for accommodating the alignment pin 188 is clearly outlined in this figure. FIG. 11 illustrates the cartridge 2 inserted into the cartridge entry port 192 and abutting the alignment pin 188 that is inserted into the optical chassis stack 180. The alignment pin 188 is also shown captured by the snap-fit element 29. In this view, the sample collection member 4 and the dilution member 6 are not shown engaged with the cartridge 2.

Figure 12:
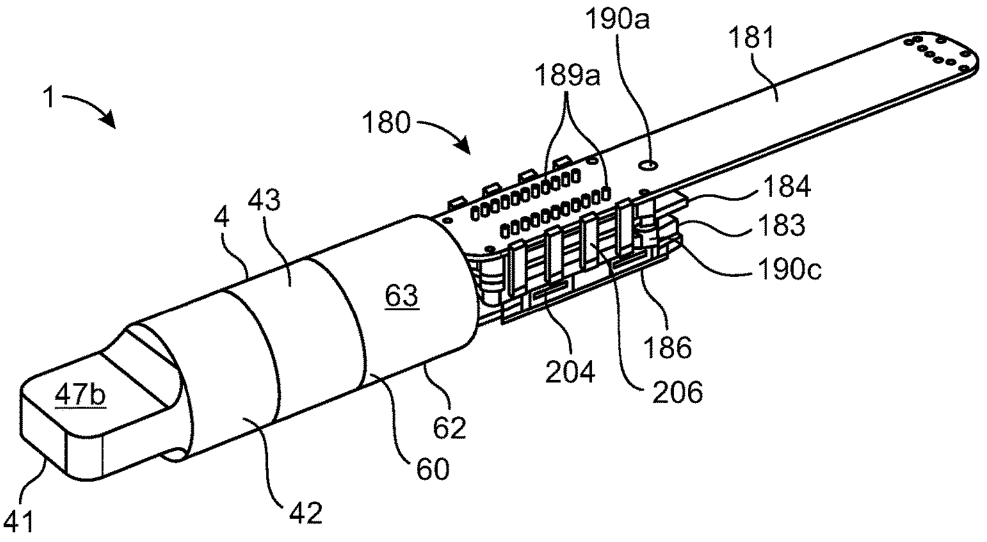
FIG. 12 illustrates the sample collection device of FIG. 1 integrated with the cartridge and chassis of the device as shown in FIG. 9.

FIG. 12 shows the sample collection member 4 engaged with the distal end 60 of the dilution member 6, which has enveloped the cartridge 2. The cartridge 2 can be seen abutting the alignment pin 188 traversing the optical chassis stack 180.

Following the manufacture of a batch of test cartridges, data associated with the batch is obtained. This data may include data such as a machine-readable optical code in the form of a barcode ID, batch coefficient data, batch expiry and assay configuration settings. This data may be compiled together for storage on a cloud database, for example into a JSON file. Assay configuration settings may include such directions as run-time, T- and C-line location, single or multiplex test, batch coefficients, dynamic read or end-point interpretation. The JSON file is then uploaded to an assay cloud database at manufacture or shortly after. The assay cloud database can contain all batch data for all manufactured tests available to the market. When a new user begins using the electronic reader device, they are directed to download an associated application to their mobile device. This application serves a number of functions including device registration, storing of results, trending of results and sharing of results, transfer of batch co-efficients and in-field firmware updates. Smartphone usage is widely established and more easily understood than often cumbersome calibration procedures. Upon first use, batch calibration data (i.e. batch coefficients) for all available tests is downloaded to the application on the user's mobile device. This batch data is then transmitted to the users' electronic reader device via Bluetooth® (or other suitable wireless technologies for transferring/transmitting data) and stored in the readers' memory until ready for use. The effect of this method is that the user has batch data available for all available tests in one background transfer. As new batch data becomes available, it is pushed to the application residing on the user's mobile device for subsequent transmission to the user's electronic reader 220 whenever the reader 220 is connected to the mobile device via Bluetooth®. In one example, the electronic reader 220 is connected to Bluetooth® each time it is turned on. Crucially, all of these data interactions happen in the background without user interaction.

As part of the overall testing system and method of the claimed invention, the inventors have developed a method for normalizing electronic reader devices against each other during the manufacturing process, such that normal manufacturing and electronic variation is reduced, and the precision of the electronic device is increased. Reducing field variation is always of benefit to those in the industry. This is achieved by optimizing sensor exposure time, such that a known baseline can be set within the reader at manufacture using a constant standard. In one aspect, the baseline standard is a white LF test strip in a cartridge. A reader value scale optimization is then undertaken by using a second standard which may be a greyscale cartridge with an industry defined reflectance value. This is captured in the memory of the reader device. In one embodiment the industry standard reflectance value is defined as being between about 15% and about 20%. Typically, the industry standard reflectance value is defined as about 18%. The effect of establishing a common baseline is that all readers are normalized to behave in the same way despite variations in manufacturing or in the components used thereby reducing variability and improving reliability which are known areas of interest and concern for those involved in the field.

Figure 13A:
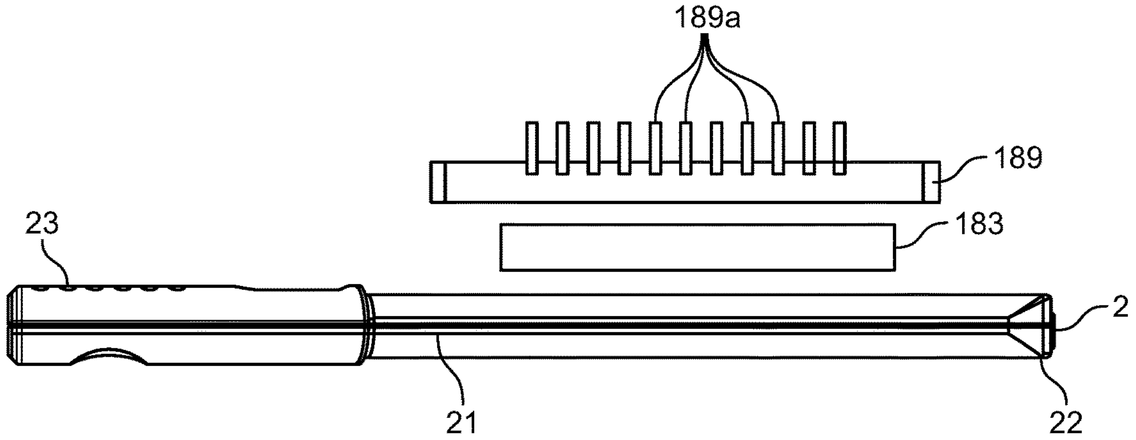
FIG. 13 illustrates (A) a side view of the relationship between the sensor, lens and cartridge of the claimed invention, and (B) a perspective view of the relationship between the sensor, lens and cartridge of the claimed invention.
Figure 13B:
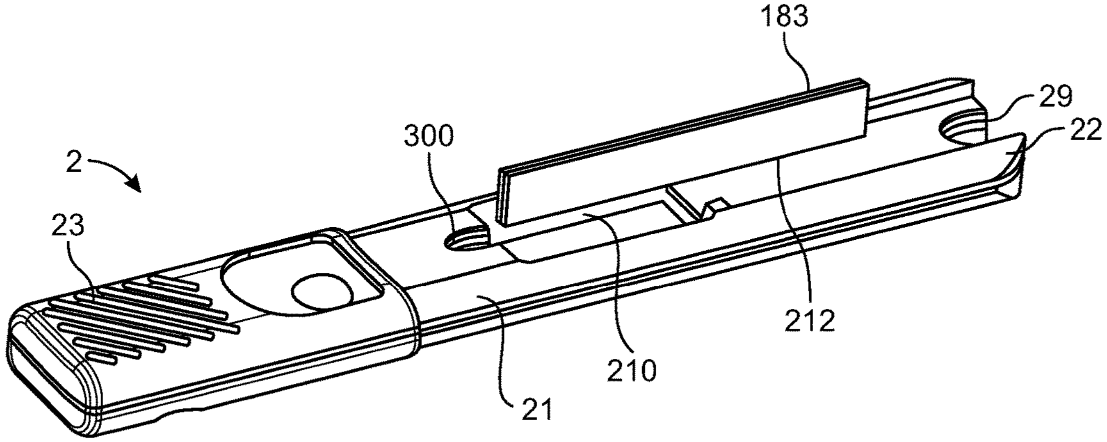

In one aspect, as shown in FIGS. 13(A) and 13(B), the linear sensor array 189 comprises two optical readers in the form of photodiodes which read a dual barcode, a single sticker or the like with two machine-readable optical codes (also known as barcodes) printed or etched on it. In such an embodiment, two photodiodes are located side-by-side at the cartridge insertion port 224 of the electronic reader 220. The first photodiode monitors how quickly the cartridge 2 is inserted into the electronic reader 220, while a second photodiode reads and interprets the machine-readable optical code. By using dual photodiodes and machine-readable optical codes together, the reader 220 can interpret the unique machine-readable optical code ID regardless of insertion speed. This differs from other benchtop LF barcode reading systems that utilize a single photodiode for machine-readable optical code reading and a motorized cartridge insertion platform to control the insertion speed (which otherwise distorts the reading/interpretation of the barcode). Other alternative systems use separate handheld scanners to their platforms to enable barcode scanning or ask the user to scan barcode data using a companion app.

Preferably, the test cartridge 2 containing the test strip 40 comprises two machine-readable optical codes 210,212, a first machine-readable optical code 212 comprising timing data and a second machine-readable optical code 210 comprising a batch identifier. For example, the test cartridge 2 may be labelled with two machine-readable optical codes 210,212 on a single label whereby one machine-readable optical code 212 is a uniform metered timing machine-readable optical code composed of uniformly spaced-apart printed lines. The uniformly spaced-apart printed lines align with and are interpreted by the first photodiode, which monitors cartridge insertion speed, while the second machine-readable optical code 210 (barcode) comprising the batch identifier encodes batch ID, batch co-efficient, manufacturing date, test ID, other information (for example, expiry date, biomarker type, species type, units of measurement, number of test lines, test line location(s), C-line location, test runtime, regions of interest, baseline location, etc.), or combinations of those, as required. Machine-readable optical code interpretation is achieved by measuring both machine-readable optical codes 210,212 simultaneously and using a decoding algorithm to reconstruct the first (timing) machine-readable optical code 212 based on the electronic reader 220 pre-programmed knowledge of the placement (including line width) of the uniformly spaced-apart lines such that it is used as a reference for interpreting the batch information on the second machine-readable optical code 210 (barcode). Once the batch identifier on the second machine-readable optical code 210 is interpreted, the batch data associated with the batch identifier is retrieved from memory. This batch data information (i.e., those coefficients) is then used to run the test. It will be appreciated that these steps can be performed by a microcontroller provided on the reader 220, which is configured to execute appropriate program instructions to perform these steps stored in the memory.

In a more detailed explanation, in order to read the machine-readable optical code (barcode) using a single photodiode as seen in other systems in the art, the movement of the cartridge is utilised under the sensor during the insertion in order to achieve a linear presentation of the machine-readable optical code (barcode). The reading of the machine-readable optical code is distorted if the insertion speed is not controlled, and thusly, mechanical motors are engaged in the devices of the prior art. These motors also contribute to the size of such devices. The inventors have found that the apparent width (or thickness) of lines on machine-readable optical code that are captured by the sensor is a function of the actual geometrical width and the speed of insertion. The inclusion of the first machine-readable optical code 212 (the timing barcode) consisting of uniformly spaced-apart lines, the image of which is pre-programmed into the electronic reader 220 allows for correction of the apparent width as measured in a distorted fashion by the sensor 189, to the actual geometrical width by comparing the readings of the two sensors. This allows the machine-readable optical codes 210,212 to be reconstructed and then decoded to give access to the data stored in the second machine-readable optical code, e.g., batch ID, test type, year etc.

The illuminating light source 204 sits below and to one side of the linear sensor array 189, and the light emitted from the light source 204 is directed to the test strip 40 via sloped sides on the cartridge viewing window on the reader 220. The optical chassis stack 180 is constructed to ensure the correct level of light will be reflected and detected by the sensor 189 to ensure an accurate analyte measurement can be made. The incorporation of the light source 204 positioned at an angle allows the sensor 189 to be positioned directly above the strip and machine-readable optical code (barcode) to maintain accurate measurement of reflected light while maintaining enough light emittance in the small form factor. The light source 204 can be placed at any angle, as long as it is capable of delivering the necessary amount of light to the test strip 40 and subsequently allowing for the linear sensor 189 to capture enough reflected light to correctly quantify the absorbance of the test line within the operating range of the test. The light source 204 at an angle is utilized here to allow the linear sensor 189 to be directly above the test strip 40. As a result, the light source 204 is placed at an angle dictated by the geometry of optical chassis stack 180 and the required characteristics of the light, such as the intensity and direction of emitted light.

Variations in electronic components and construction of the optical chassis stack 180 can lead to variation in the performance of the reader 220. While tight material and manufacturing tolerances can control for mechanical variation, the reader 220 to reader 220 calibration procedure of the claimed invention minimises electronic component variation. The proposed form factor incorporating the optical chassis stack 180 significantly reduces the devices' size, while achieving high resolution for test result interpretation and enabling integrated barcode scanning for ease of use.

In one example, the LF test cartridge 2 geometry is designed in such a way that prevents incorrect insertion of the cartridge 2 into the cartridge entry port 224 of the reader 220. The asymmetrical profile along the length of the cartridge 2 (the configuration of the proximal end 22 and distal end 23) will prevent the cartridge being inserted back to front into the device 1 and the sample collection member 4/dilution member 6. For example, as shown in FIG. 13(A), 13(B), the proximal end 22 has the snap-fit element 29 configured to engage with the alignment pin 188. The keyed top surface of the proximal end 22 of the cartridge will prevent the cartridge being inserted upside down.

In a further aspect, error reduction is improved upon through an error checking system executed by the micro-controller by means of program stored in the memory. The linear sensor array 189 is used to check cartridge 2 insertion status, notifying the user that if the cartridge 2 has been inserted incorrectly or incompletely. This is achieved by characterizing scan features and setting tolerances within the software around how they should appear to the optical sensor. Dirt or particulate matter on the lens 183 can also be identified. In this scenario, the user would be notified to clean the lens 183. To achieve this, a scan of the empty cartridge port 186 is saved to memory at factory. Whenever a cartridge scan is taken, the scan is saved to memory. When a user removes a cartridge 2 from the reader 220, a scan of the empty cartridge port 186 is taken. The cartridge scan and empty cartridge port scan is compared. If a feature is present in both the cartridge scan and the empty cartridge port scan, then there is dirt or an obstruction on the lens 183. If the feature is only present in the empty cartridge port scan, then the dirt is on the cartridge port 186 and the user is not notified to clean the reader lens 183.

It is also possible for the user to send the results of any test to the cloud-based database for storage and subsequent analysis. In this way, or by other methods, by comparing results from different locations, or from the same location over time, the growth, spread or containment of, for example, infection, can be monitored. This information could be very valuable at local, regional, national and international levels, for example to monitor patterns of an outbreak of a disease. The information can also be used by the user to monitor their health status over time. A general practitioner of medicine or a local hospital could also receive updated information from a user so that their medical record is a more complete picture of their overall health status.

The POC device 1 described herein offers advantages over the current protocols and POC devices in that it readily provides a quick, real-time and accurate insight into the host response by analysing markers of, for example, the immune response. The POC device 1 described herein is enabled and appropriate for settings in clinical, domestic and veterinarian settings.

Some of the other advantages of the POC device 1 described herein is that it provides a more accurate, informative and rapid real-time understanding of a patient's health status than that traditionally provided by the current POC devices; the POC device 1 can be used for pro-active health management with more flexibility for analysing different targets simultaneously than currently available in current POC devices; the device 1 is an all-in-one integrated device with the sample collection, dilution and testing being carried out in a single device; the flexibility for modification to accommodate further biomarkers in the form of multiplex or single plex disposables which could form a discrete component or a fully integrated, combined feature.

The optical chassis stack 180 described herein is composed of elements for capturing an image, for example, an image of a lateral flow strip. The second PCB 184 contains several illuminating light sources 204, such as light emitting diodes (LEDs), which are the sole light source within the optical chassis stack 180 when a cartridge is inserted into the reader 1. The duration of illumination (integration factor) is the primary determinant of the amount of light reaching the linear sensory array 189. The integration factor is determined as described in this application as part of a calibration method. The light emitted by the illuminating light source 204 travels downwards through the optical chassis stack 180 and illuminates the test strip 40 within the cartridge 2. The light source 204 can have one or more colours to allow for optimised detection of multiple different detection particles. In one example, the light source 204 is green and optimised for the detection of red particles absorbing in the green range at a wavelength of about 497-770 nm. Alternatively, the light source 204 is blue and optimized for detecting orange particles absorbing light in the blue range about 450-500 nm. In a further example, the light source 204 is orange and therefore optimized for detecting blue particles in the range about 585-620 nm. This light is reflected by the cartridge 2 and the test strip 40 within. The surfaces with higher absorbance, such as dark lines on a test strip 40, reflect less light, while surfaces with low absorbance properties, such as the white background of the test strip 40, reflect more light. The reflected light then travels upwards though the optical chassis stack 180 and enters the bottom surface of the lens 183. Light then traverses internally though the lens 183 and emerges through the upper surface of the lens 183. The addition of the lens 183 facilitates image transfer from the object (e.g., test strip) to the sensor array 189 and results in an improvement in focus of the sensor array 189 creating a more precise image. In systems that do not utilize a lens 183, light reflecting from below may scatter across the sensors array 189. As such, the device 1 is rendered more accurate by the presence of the lens 183, i.e., a more accurate representation of the test strip 40 is generated.

When the lens 183 takes the form of a series of rod lenses forming a collimator into which the light travels, light is directed directly into the linear sensor array 189. The advantage being a concentration of reflected light. A further advantage is a reduction of interference from surrounding light. When the collimated light enters the linear sensor array 189, it is quantified by sensing elements within, which may be light sensitive capacitors. The linear sensor array 189 may use a charge-coupled device (CCD) or an active-pixel sensor (CMOS sensor), for example, where the sensing elements are made of light-sensitive capacitors which convert photons into electrons. The resulting electrical charge is then read out by the sensor circuitry from each sensing element. The digital output of the linear sensor array 189 then contains an image of the cartridge 2 and/or test strip 40 made of a single row of pixels. In one aspect, the number of pixels is 3648.

The lens holder 182 may contain two or more lenses 183, and up to 200 lenses, arranged in a single row in such a way that the individual images produced by each lens 183 overlap, forming a continuous image of the surface below the lens 183. This lens 183, in this capacity, is an image transfer device with a unit magnification, resulting in 1:1 image transfer between the cartridge 2 below and the linear sensor array 189 above. The use of a large imaging sensor with length equal to the object being imaged produces an imaging system with a high degree of accuracy. In other systems of the prior art, the sensor is often small, requiring a lens that reduces the ratio between the sensor and the object to be imaged. The negative affect of this is less accuracy owing to background noise introduced by the small size of the sensing elements and optical errors introduced due to the lensing effect, i.e., the transformation of the image so that it can captured by the sensor smaller than the object.

The lens 183 array is maintained in the correct position by the lens holder 182 located between the linear sensor array 189 and the cartridge 2 to ensure that the working distance on each side of the lens 183 is maintained. The short total conjugate (distance between the linear sensor array 189 and the lens 183, the distance between the lens 183 and the object to be captured, and the height of the lens 183 itself) of this optical system is facilitated by the lens 183 and contributes and enables the compact design of the system of the invention, thereby increasing POC utility.

The positioning of the illuminating light source 204 with respect to the lens 183 is important in preventing exogenous and contaminating light from entering the upwards light path of the optical chassis stack 180, which could impact the accuracy of the system. Exogenous and contaminating light is any light reaching the sensor that has not been reflected by the cartridge 2 and/or the strip 40. This light might occur due to light reflecting from other surfaces within the system or from LED light that directly enters the lens 183. Light may also travel from outside of a system if the system is not isolated. Both the lens holder 182 and the lens 183 protrude though a slot 400 in the second PCB (184) (see FIG. 15) resulting in the illuminating light source 204 being positioned higher in the optical chassis stack 180 than the bottom of the lens 183/lens holder 182 (but below the top surface of the lens 183). The light emitted by the illuminating light source 204 therefore travels downwards parallel to the lens 183, and only after it is reflected by the surfaces of the cartridge 2 can it enter the lens 183. The surfaces inside the optical chassis stack 180, such as the chassis 185, the lens holder 182 and the second PCB 184, may be made of dark-coloured materials to further prevent exogenous light reflecting by increasing the absorbance of the material.

A significant issue relating to point of care testing is accuracy, i.e., sensitivity and specificity and system variation. All components of a system can contribute to accuracy and variation.

In lateral flow, the assembly and positioning of components within the reading devices can introduce inaccuracies in detection and contribute to variation in results. Two contributors to these inaccuracies are lateral movement and torsion or twisting movements of the device 1 during use. To overcome this, the device 1 of the claimed invention includes the alignment pin 188, positioned vertically through the optical chassis stack 180. The alignment pin 188 will hold the components of the optical chassis stack 180 in position relative to each other, and also hold the cartridge 2 in position when inserted into the device 1, such that lateral/sideways motion and torsion/twisting movement of the cartridge 2 is prevented.

Figure 16:
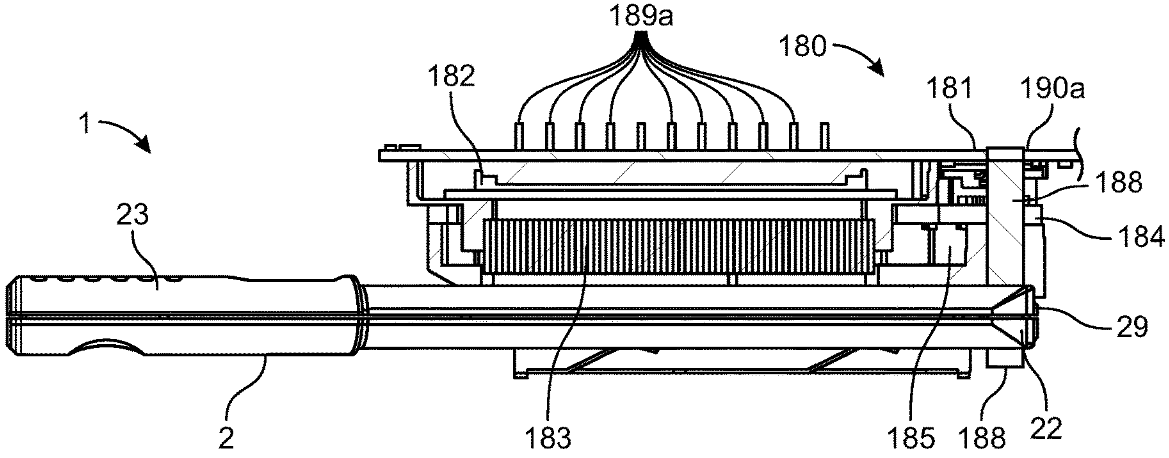
FIG. 16 illustrates a cross-sectional view of the chassis stack with a cartridge engaged as shown in FIG. 12.

On the bottom of the optical chassis stack 180, the alignment pin 188 positions the inserted cartridge 2, which clips onto the alignment pin 188 with the snap-fit element 29 located at the proximal end 22 of the cartridge 2 (see FIG. 16). Correct positioning of the elements within the optical chassis stack 180 increases the accuracy of the system by optimising the positioning of the image such that introduction of variation is reduced and focus with respect to the linear sensor array 189 is improved.

The invention further improves accuracy and variation through the structure of the optical chassis stack 180, which guides the insertion of the cartridge 2 to the alignment pin 188. Furthermore, the cartridge port 186, which is located at the base of the optical chassis stack 180 and accommodates the cartridge 2, has a plurality of springs 208. The springs 208 control the vertical position of the cartridge 2 and controls the defined distance between the surface being imaged and the bottom of the lens 183 by ensuring the cartridge 2 is in continuous contact with the bottom of the chassis 185.

The significance of two PCBs 181,184 relate to the optimised positioning of the illuminating light source 204 relative to the linear sensor array 189. Other devices often put the light source(s) on the same PCB to the disadvantage of the overall form factor, as it requires an increased PCB size and therefore increased form factor. The device 1 of the claimed invention achieves a smaller form factor in this regard through the positioning of the illuminating light source 204 on the second PCB 184.

The device 1 of the claimed invention was compared to an off-the-shelf reader that does not contain the features of the claimed invention (LFDR Device, Forsite Ltd, York, United Kingdom. Three readings were taken for each of three cartridge insertions and accuracy and precision data was calculated and presented in Table 1 to compare the performance of the two devices. The device 1 of the claimed invention demonstrated better performance than the off-the shelf device, with improved precision and accuracy.

TABLE 1

Precision Comparison of the system of the claimed invention versus an off-the-shelf system.

| Accuracy (%) | | Precision (% CV) | |
|---|---|---|---|
| Device of Invention | Off the shelf Device | Device of Invention | Off the shelf Device |
| 96.4 | 88.5 | 3.69 | 11.97 |

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g., CD ROM, or magnetic recording medium, e.g., a memory stick or hard disk. The carrier may be an electrical or optical signal which may be transmitted via an electrical or an optical cable or by radio or other means.

The information determined in the determination system can be read by the storage system. As used herein the "storage system" is intended to include any suitable computing or processing apparatus or other device configured or adapted for storing data or information. Examples of an electronic apparatus suitable for use with the present invention include a stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage system is adapted or configured for having recorded thereon growth response information and growth response fingerprint information. Such information may be provided in digital form that can be transmitted and read electronically, e.g., via the Internet, on diskette, via USB (universal serial bus) or via any other suitable mode of communication.

The storage system may have reference growth response fingerprint information stored thereon. As used herein, "stored" refers to a process for encoding information on the storage device. In one embodiment the reference data stored in the storage device to be read by the comparison module is compared, e.g., comparison of a query cell-specific growth response fingerprint with a set or panel of reference growth response fingerprints.

The "comparison system" can use a variety of available software programs and formats for the comparison operative to compare query growth response fingerprint with reference growth response fingerprints and identify a "match". In one embodiment, the comparison module is configured to use pattern recognition techniques to compare information from one or more entries to one or more reference data patterns. The comparison module may be configured using existing commercially-available or freely-available software for comparing patterns and may be optimized for particular data comparisons that are conducted. The comparison module provides computer readable information related to the genotype of the sample. Preferably, the comparison system employs a computational model for comparison purposes.

The comparison module, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware, as may be necessary should the server be distributed over two or more separate computers. In one embodiment, the World Wide Web server supports a TCP/IP protocol. Local networks such as this are sometimes referred to as "Intranets."

An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module typically provides a computer readable comparison result that can be processed in computer readable form by predefined criteria, or criteria defined by a user, to provide a content based in part on the comparison result that may be stored and output as requested by a user using a display system.

In one embodiment of the invention, the content based on the comparison result is displayed on a computer monitor. In one embodiment of the invention, the content based on the comparison result is displayed through printable media. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, California, or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

Figure 14:
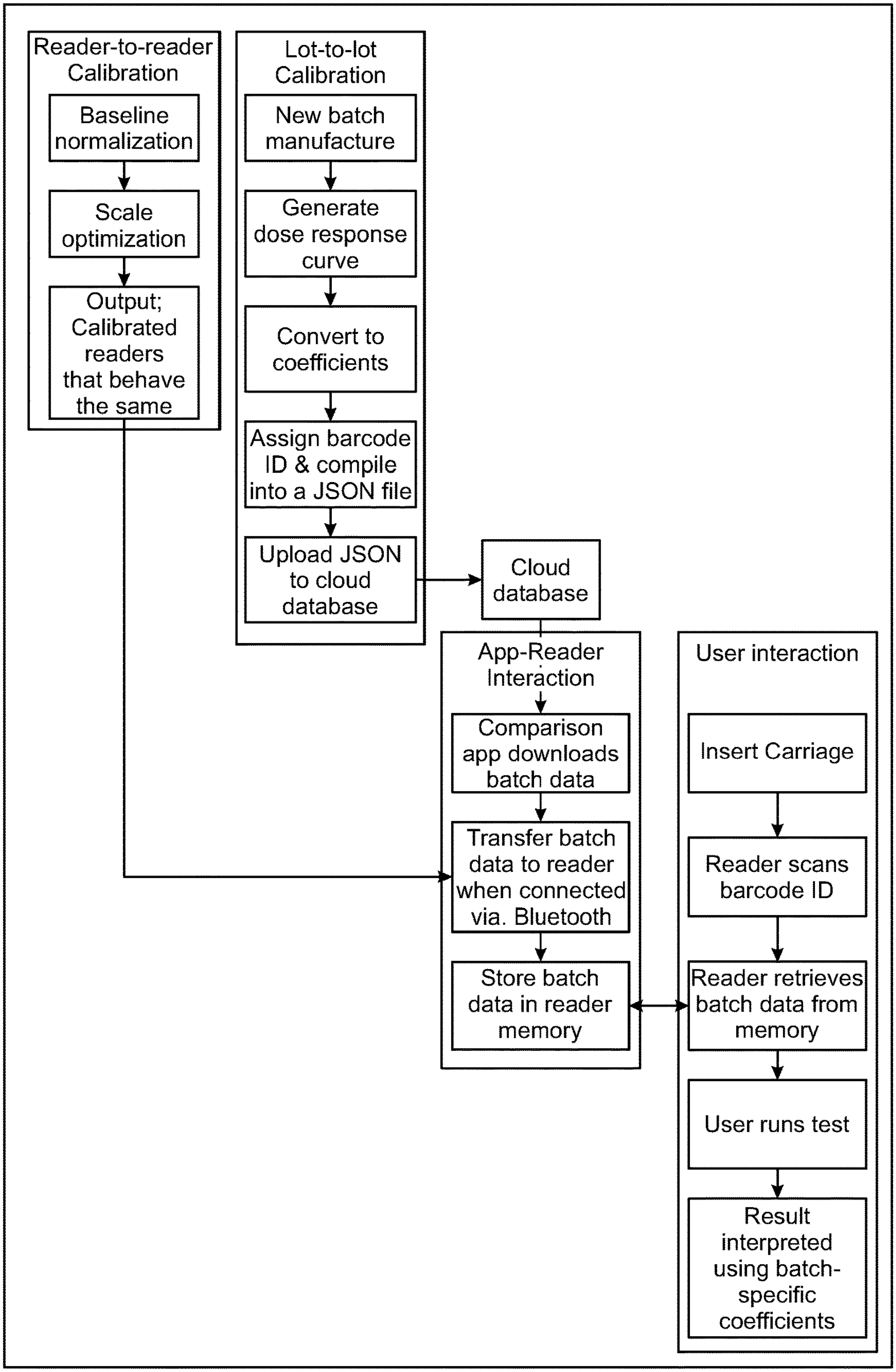
FIG. 14 is a flowchart illustrating the calibration coefficient workflow to calibrate the device of the claimed invention.

The seamless and automated batch to batch calibration process (described in FIG. 14) involves cloud transfer of batch data to the users' phone and further transfer of that data to the users' electronic reader in the background without any interaction requirements from the user. This enables the user to use the testing platform without performing calibration specific procedures themselves. This reduces the introduction of human error and improves user confidence by avoiding the uncertainty which often accompanies unfamiliar procedures.

Another benefit of the system is a reduction of issues associated with lost batch or chip data. In current methods, if a user loses, damages or is not provided with the memory chip, testing cannot be performed until the chip is replaced by the manufacturer. This issue is overcome with the proposed solution as batch data is readily retrievable from the assay cloud database.

A further benefit of the system is that the device undertakes differentiation of the type of tests being inserted itself based on the barcode data creating a smooth and seamless user experience. This is different from current methods which require different test specific memory chips to be inserted for different analyte test cartridges prior to running a test.

In the same invention, batch traceability and batch-to-batch calibration are enabled during manufacture. This is achieved by assigning each batch a unique readable optical code ID. Batches are typically characterised at manufacture whereby a dose-response curve is generated, then converted to coefficients. Coefficients are ultimately used to calculate the result by assigning a biomarker (analyte) value against the test output such as against test line signal intensity. In this invention a unique 5-digit machine readable optical code, 1D 2 of 5 interleaved is applied as a label to the cartridge. The machine-readable optical code encoded on each cartridge corresponds to the batch from which it was manufactured. An example of a format is YYBBT (year-year, batch-batch, test). Critically in this invention, when a cartridge 2 is inserted into the electronic device 1, the machine-readable optical code comprising the batch ID is read by the same sensor 189 that detects, analyses and quantifies the test strip 40 in a single insertion without the need for batch-to-batch calibration specific materials. Upon reading the batch ID, the device 1 retrieves corresponding batch data from memory and uses that information (i.e. those coefficients) to run the test as previously described.

A further benefit of the system is that the machine-readable optical code is not affected by insertion speed, whereby the machine-readable optical code is distorted due to the speed of insertion of the cartridge 2. This is because the machine-readable optical code interpretation is undertaken when the cartridge 2 is fully inserted rather than as the cartridge 2 is being inserted as is seen in other systems.

In the specification, the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments hereinbefore described but may be varied in both construction and detail.

The invention claimed is:

1. A portable point of care device for use in testing a biological sample, the device comprising: a sample collection member, a test cartridge, a reader, and an alignment pin; the test cartridge comprising a housing within which is a test strip, a distal end and a proximal end, the proximal end adapted to engage with a cartridge entry port of the reader; the sample collection member comprising a distal end, a sample chamber and a proximal end adapted to connect to the distal end of the test cartridge; and the reader comprising a casing within which is housed an optical chassis stack, and the cartridge entry port configured to accept the test cartridge; wherein the optical chassis stack further comprises a first printed circuit board (PCB) in communication with a lens holder, which accommodates a lens, a second PCB in communication with the lens holder, a chassis in communication with the second PCB, a cartridge port with springs in communication with the chassis, and a linear sensor array in communication with the first PCB; wherein the optical chassis stack further comprises a shaft traversing therethrough from the first PCB to the chassis, and configured to accommodate the alignment pin, wherein the alignment pin travels down through the shaft that continues down through the components of the optical chassis stack from the first PCB to the chassis.

2. A device according to claim 1, wherein the shaft comprises at least three or four engagement mechanisms, wherein a first engagement mechanism is an aperture at the entrance to the shaft on the first PCB; a second engagement mechanism is an aperture located on the second PCB; and a third engagement mechanism and, a fourth engagement mechanism are snap-fit elements located on the chassis that engage with the alignment pin.

3. A device according to claim 1, wherein the second PCB comprises an aperture and an illuminating light source.

4. A device according to claim 3, wherein the illuminating light source sits below and to one side of the linear sensor array.

5. A device according to claim 3, wherein the light emitted from the light source is directed to the test strip at an angle via sloped sides on a cartridge window.

6. A device according to claim 1, wherein the test cartridge comprises a first machine-readable optical code comprising timing data and a second machine-readable optical code comprising a batch identifier.

7. A device according to claim 1, wherein the linear sensor array comprises at least two optical readers in the form of a first optical reader and a second optical reader; wherein the first optical reader is configured to determine a speed that the test cartridge is inserted into the reader by reading and interpreting a first machine-readable code, and the second optical reader is configured to read and interpret a second machine-readable optical code on the test cartridge.

8. A device according to claim 1, wherein the lens is in the form of a lens array.

9. A device according to claim 1, wherein the lens is a rod lens.

10. A device according to claim 1, wherein inner surfaces of the optical chassis stack are coated with, or are partly formed with, a light-absorbing paint or a light-absorbing material.

11. A device according to claim 1, in which the test strip comprises a sample pad, a conjugate pad, a testing membrane and a wicking pad.

12. A device according to claim 1, in which the test strip is impregnated with one or more reagents that react with one or more target molecules in the test sample, wherein the reagent is selected from an antibody, a labelled antibody, a nucleic acid, a labelled nucleic acid, a protein scaffold, a labelled protein scaffold, a peptide aptamer, a labelled peptide aptamer, and RNA aptamer, a labelled RNA aptamer, or a combination thereof.

13. A device according to claim 12, in which the test strip is in a sandwich format and consists of a nitrocellulose membrane upon which an antibody to the target molecule and a control antibody have been immobilised.

14. A device according to claim 1, in which the sample collection member collects bodily fluid by capillary action, aspiration or under vacuum.

15. A device according to claim 14, in which the test cartridge further comprises at least one machine-readable optical code encoding information that is read by at least one optical reader in the linear sensor array.

16. A device according to claim 15, wherein result data from the test cartridge can be transmitted to a remote device over a wireless communication means for display by the remote device, and wherein the remote device is a mobile phone device or electronic tablet device.

17. The device according to claim 1, wherein the reader further comprises a microcontroller and a memory coupled with the microcontroller, wherein the memory comprises executable program instructions to configure the microcontroller to perform the steps of:

receiving by the reader, via wireless communication, batch data from an application associated with the reader residing on a mobile device; and storing the received batch data in the memory.

18. A device as claimed in claim 1 configured to (i) monitor an immune status of an individual, or (ii) for assess an infection status of an individual, or (iii) predict a health event in an individual, or (iv) determine whether an individual is suffering from a disease, or a combination thereof.

19. A system comprising:

the device of claim 1; and a cloud database for storing batch data obtained during manufacture of a batch of the test cartridges; and an application associated with the reader downloadable to a mobile user device, wherein the application is configured to receive batch data transmitted from the cloud database and result data transmitted by the reader and to transmit batch data to the reader.

20. The system according to claim 19, wherein batch data obtained during manufacture of a batch of the test cartridges is uploaded to the cloud database, wherein the application is further configured to send result data to the cloud database.

* * * * *